(12) United States Patent
Taniguchi

(10) Patent No.: US 10,335,119 B2
(45) Date of Patent: Jul. 2, 2019

(54) ULTRASOUND IMAGE DIAGNOSTIC APPARATUS

(71) Applicant: Konica Minolta, Inc., Tokyo (JP)

(72) Inventor: Tetsuya Taniguchi, Hachioji (JP)

(73) Assignee: KONICA MINOLTA, INC., Tokyo (JP)

( * ) Notice: Subject to any disclaimer, the term of this patent is extended or adjusted under 35 U.S.C. 154(b) by 705 days.

(21) Appl. No.: 15/145,886

(22) Filed: May 4, 2016

(65) Prior Publication Data

US 2016/0338670 A1 Nov. 24, 2016

(30) Foreign Application Priority Data

May 21, 2015 (JP) .................. 2015-103842

(51) Int. Cl.
*A61B 8/00* (2006.01)
*G01S 7/52* (2006.01)
*A61B 8/08* (2006.01)

(52) U.S. Cl.
CPC .......... *A61B 8/5207* (2013.01); *G01S 7/5202* (2013.01); *G01S 7/52038* (2013.01); *A61B 8/4405* (2013.01); *A61B 8/4483* (2013.01); *G01S 7/52046* (2013.01)

(58) Field of Classification Search
CPC ... A61B 8/4405; A61B 8/4483; A61B 8/5207; G01S 7/5202; G01S 7/52038; G01S 7/52046

See application file for complete search history.

(56) References Cited

U.S. PATENT DOCUMENTS

| 2006/0058677 A1* | 3/2006 | Okada ..................... | A61B 8/00 600/459 |
| 2014/0249418 A1* | 9/2014 | Taniguchi ............... | A61B 8/14 600/447 |

FOREIGN PATENT DOCUMENTS

| JP | 2002301068 A | 10/2002 |
| JP | 2003310609 A | 11/2003 |
| JP | 2014168555 A | 9/2014 |

* cited by examiner

*Primary Examiner* — Michael T Rozanski
(74) *Attorney, Agent, or Firm* — Lucas & Mercanti, LLP

(57) ABSTRACT

An ultrasound image diagnostic apparatus includes an ultrasound probe, a transmitter and an image generator. The ultrasound probe transmits ultrasound to a subject and generates a reception signal. The transmitter drives the ultrasound probe to transmit ultrasound that satisfies the following requirements: a wave packet duration is equivalent to or more than the length of 1.5 waveforms at the lower limit frequency of the −6 dB transmission bandwidth of the ultrasound probe; signal intensity of frequency components in the −6 dB transmission bandwidth has a standard deviation of 6 or less; and lower limit frequency components in the −6 dB transmission bandwidth have a signal intensity of −8 [dB] or higher, the signal intensity being normalized with respect to the maximum intensity of 0 [dB]. The image generator extracts harmonic components from the reception signal and generates ultrasound image data.

8 Claims, 26 Drawing Sheets

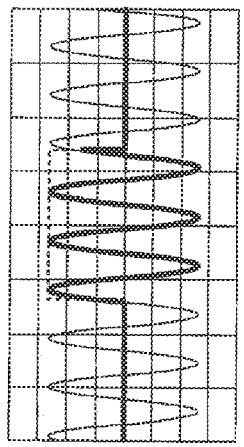
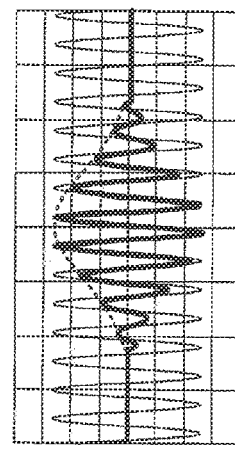
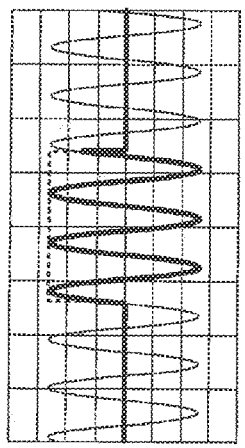
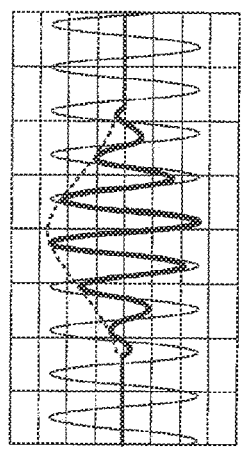
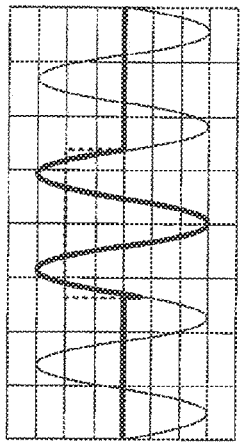
FIG. 7A
FIG. 7B

ULTRASOUND IMAGE DIAGNOSTIC APPARATUS

This U.S. patent application claims priority to Japanese patent application No. 2015-103842 filed on May 21, 2015, the entire contents of which are incorporated by reference herein.

BACKGROUND OF THE INVENTION

1. Field of the Invention

The present invention relates to an ultrasound image diagnostic apparatus.

2. Description of Related Art

Ultrasound diagnosis provides information about the pulsation of a heart or movements of a fetus just by a simple operation that involves application of an ultrasound probe to the surface of a body. The ultrasound diagnosis, which is highly safe for human bodies, is available in repeated inspections.

In such an ultrasound diagnostic imaging technique, a satisfactory image having a high contrast can be produced from the harmonic frequency components (for example, frequency 2f0 or 3f0) of the fundamental frequency component (frequency f0) of a transmission signal. Such an imaging technique is referred to as tissue harmonic imaging.

The main cause of these harmonic components is nonlinear distortion generated during propagation of ultrasound through the body of a subject. In other words, ultrasound signals applied to the living body is distorted during propagation through the tissue due to a nonlinear response from the tissue, which increases harmonic components. As a result, the echo signal contains the component of the frequency 2f0, which is twice the fundamental frequency f0, and the component of the frequency 3f0, which is three times the fundamental frequency f0.

In the tissue harmonic imaging, one of the traditional methods for extracting harmonic components from an echo signal is filtering. This method involves the extraction of the harmonic component of the frequency 2f0 from a reception signal with a bandpass filter having a central frequency of, for example, 2f0. Another example is a pulse inversion technique. The pulse inversion technique involves the transmission of a signal of a first transmission waveform and another signal of a second transmission waveform having the reverse polarity to the polarity of the first transmission waveform at a certain time interval and phasing addition of their echo signals to suppress the fundamental frequency component and thus emphasize the second harmonic component. The suppression of the fundamental frequency component requires the transmitter that transmits a first transmission waveform and a second transmission waveform having the reverse polarity to the polarity of the first transmission waveform to have a high positive-negative symmetricity of an excitation signal.

Unfortunately, harmonic components of an ultrasound signal, which have a higher frequency than the fundamental component, are more vulnerable to attenuation during propagation and have low transmission or penetration of the eco signal from deep sites. A lower central frequency f0 of fundamental waves can make harmonic components less vulnerable to attenuation and thus improve penetration, but reduces resolution, as is known in the art.

Of these two methods, the filtering method, which involves a uniform cutting of the low-frequency region without any distinction between the fundamental and harmonic waves, has a significant impact on the cutting, thus produces a narrow bandwidth after extraction and is generally inferior in the quality of the resulting images to the pulse inversion technique. Accordingly, the pulse inversion technique is the mainstream except for low-priced devices.

In recent years, methods for enhancing the penetration while maintaining the resolution have been proposed in the pulse inversion technique. Such proposals include the use of subharmonics of a frequency lower than that of the second harmonic (refer to JP 2002-301068A) or the generation of harmonics of a frequency in a range from f0 to 2f0 (twice the frequency of f0) (refer to JP 2003-310609A). Unfortunately, these methods still require a transmitter to have a high positive-negative symmetricity of an excitation signal.

In addition, there is an increased demand, not for the traditional single-frequency transmission, but for transmission of more complex temporal waveforms containing multiple frequencies or involving frequency transition. Such complex temporal waveforms cannot be controlled by low-priced transmitters capable of only transmitting signals having three levels of voltage (+HV/GND/−HV) or five levels of voltage (+HV/+MV/GND/−MV/−HV) and require adoption of a transmitter capable of driving multiple levels of voltage or waveform shaping at a peripheral circuit. Such a tendency further precludes reductions in cost and sizes of such transmitters.

As a result of extensive studies, the present inventor has successfully found a method for solving the above-mentioned problems. More specifically, the inventor can provide an ultrasound diagnostic apparatus capable of acquiring harmonic images with significantly high resolution, even with a transmitter capable of addressing only five or less levels of voltage, by setting the peak intensity of power spectrum at the frequency of a transmission signal to an appropriate value (See JP 2014-168555A).

The ultrasound diagnostic apparatus disclosed in JP 2014-168555A is usable as it can acquire high-resolution images and has high penetration. Unfortunately, the disclosed apparatus tends to have reduced resolution for deep sites. There is a demand for maintaining a high resolution and a high signal-to-noise ratio for shallow sites and improving resolution for deep sites to acquire highly uniform harmonic images for the shallow to deep sites.

One of the methods for generating harmonic images for deeper sites is to increase driving voltage. Such an increase in driving voltage requires a high-capacity power supply and an ultrasound image diagnostic apparatus having a high voltage resistance. This configuration results in an increase in size and cost of the apparatus and cannot be achieved by a low-priced small apparatus. The increase in voltage also increases the risk of depolarization or insulation breakdown of the piezoelectric elements of an ultrasound probe. Thus, a method that does not involve an increase in voltage is required for the visualization of deeper sites.

One of the methods for enhancing a signal-to-noise ratio that do not involve an increase in voltage is a pulse compression technique. The pulse compression technique involves the transmission of long pulses, such as coded signals or chirp waves, and the application of a matched filter to received signals to acquire short pulses. Such a pulse compression technique is, in principle, applicable only to fundamental imaging, not to harmonic imaging.

The harmonic imaging uses a method for generating a long pulse just by concatenating traditional transmission waveforms. Unfortunately, a excitation time exceeding the length of 1.5 waveforms at the lower limit frequency of the −20 dB bandwidth of an ultrasound probe reduces the resolution of images which are acquired by generating long pulses from transmission signals, thus precluding the acquisition of ultrasound images that satisfy the above-mentioned requirements.

SUMMARY OF THE INVENTION

It is the object of the present invention to facilitate the acquisition of uniform high-quality ultrasound images from the shallow to deep sites.

In order to realize the above object, according to a first aspect of the present invention, there is provided an ultrasound image diagnostic apparatus including:

an ultrasound probe which transmits transmission ultrasound (hereinafter simply referred to as "ultrasound") to a subject, receives reflected ultrasound, and generates a reception signal;

a transmitter which generates an excitation signal and outputs the excitation signal to the ultrasound probe to instruct the ultrasound probe to generate the ultrasound;

a receiver which receives the reception signal from the ultrasound probe; and an image generator which extracts harmonic components from the reception signal and generates ultrasound image data based on the harmonic components, wherein the transmitter drives the ultrasound probe with the excitation signal to instruct the ultrasound probe to transmit the ultrasound that satisfies the following requirements: a wave packet duration is equivalent to or more than the length of 1.5 waveforms at the lower limit frequency of the −6 dB transmission bandwidth of the ultrasound probe; signal intensity of frequency components in the −6 dB transmission bandwidth has a standard deviation of 6 or less; and lower limit frequency components in the −6 dB transmission bandwidth have a signal intensity of −8 [dB] or higher, the signal intensity being normalized with respect to the maximum intensity of 0 [dB], and wherein the image generator generates the ultrasound image data based on the harmonic components in the reception signal obtained after the transmission of the ultrasound.

According to a second aspect of the present invention, there is provided an ultrasound image diagnostic apparatus including:

an ultrasound probe which transmits ultrasound to a subject, receives reflected ultrasound, and generates a reception signal;

a transmitter which generates an excitation signal and outputs the excitation signal to the ultrasound probe to instruct the ultrasound probe to generate the ultrasound;

a receiver which receives the reception signal from the ultrasound probe; and an image generator which extracts harmonic components from the reception signal and generates ultrasound image data based on the harmonic components, wherein the transmitter drives the ultrasound probe with the excitation signal that satisfies the following requirements: excitation time is equivalent to or more than the length of 1.5 waveforms at the lower limit frequency of the −6 dB transmission bandwidth of the ultrasound probe, signal intensity of frequency components in the −6 dB transmission bandwidth has a standard deviation of 7 or less; and signal intensity of lower limit frequency components in the −6 dB transmission bandwidth is 10 [dB] or higher.

Preferably, the transmitter synthesizes AM- or FM modulated multiple temporal waveforms into the excitation signal.

Preferably, the transmitter assigns voltage to a waveform into which AM- or FM modulated multiple temporal waveforms are synthesized in accordance with the number of voltage levels of the transmitter, stores the waveform information, and generates the excitation signal based on the stored waveform information.

According to a third aspect of the present invention, there is provided an ultrasound image diagnostic apparatus including:

an ultrasound probe which transmits ultrasound to a subject, receives reflected ultrasound, and generates a reception signal;

a transmitter which generates an excitation signal and outputs the excitation signal to the ultrasound probe to instruct the ultrasound probe to generate the ultrasound;

a receiver which receives the reception signal from the ultrasound probe; and an image generator which extracts harmonic components from the reception signal and generates ultrasound image data based on the harmonic components, wherein the transmitter drives the ultrasound probe with the excitation signal that satisfies the following requirements: excitation time is equivalent to or more than the length of 1.5 waveforms at the lower limit frequency of the −6 dB transmission bandwidth of the ultrasound probe, duration of parts of the excitation signal is converted into a frequency with duration of each of the parts regarded as 0.5 waveforms, the converted frequency is normalized with respect to the central frequency of the −6 dB transmission and reception bandwidth of the ultrasound probe, and the normalized frequency has a standard deviation ranging from 0.1 to 0.3.

Preferably, at least one of a first part and a last part of the excitation time is a maximum part of all parts.

Preferably, all parts between the first and the last parts of the excitation time are shorter than both the first and last parts.

Preferably, the transmitter outputs multiple excitation signals having different waveforms at certain intervals on one scanning line; and the image generator extracts harmonic components through calculation of the reception signals generated in response to reflected ultrasound corresponding to ultrasound generated in response to the multiple excitation signals, and generates ultrasound image data based on the harmonic components.

BRIEF DESCRIPTION OF THE DRAWINGS

The present invention will become more fully understood from the detailed description given hereinbelow and the appended drawings which are given byway of illustration only, and thus are not intended as a definition of the limits of the present invention, and wherein:

FIG. 7A illustrates traditional waveform synthesis;

FIG. 7B illustrates waveform synthesis according to the embodiment;

DETAILED DESCRIPTION OF THE PREFERRED EMBODIMENT

Figure 1:
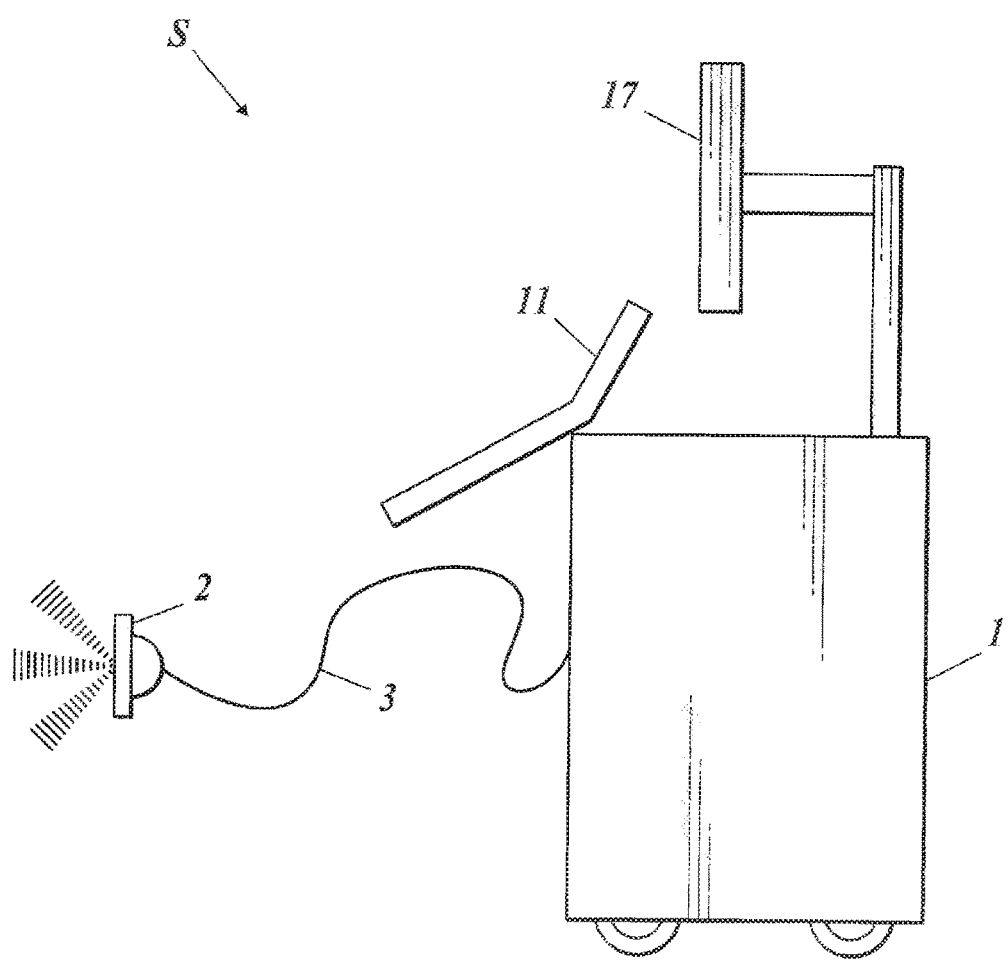
FIG. 1 is an external view of an ultrasound image diagnostic apparatus according to an embodiment of the present invention.

Embodiments of the present invention will now be described with reference to the attached drawings. The embodiments shown in the drawings should not be construed to limit the present invention. Components having the same functions or configurations are denoted by same reference numerals without redundant description.

Figure 2:
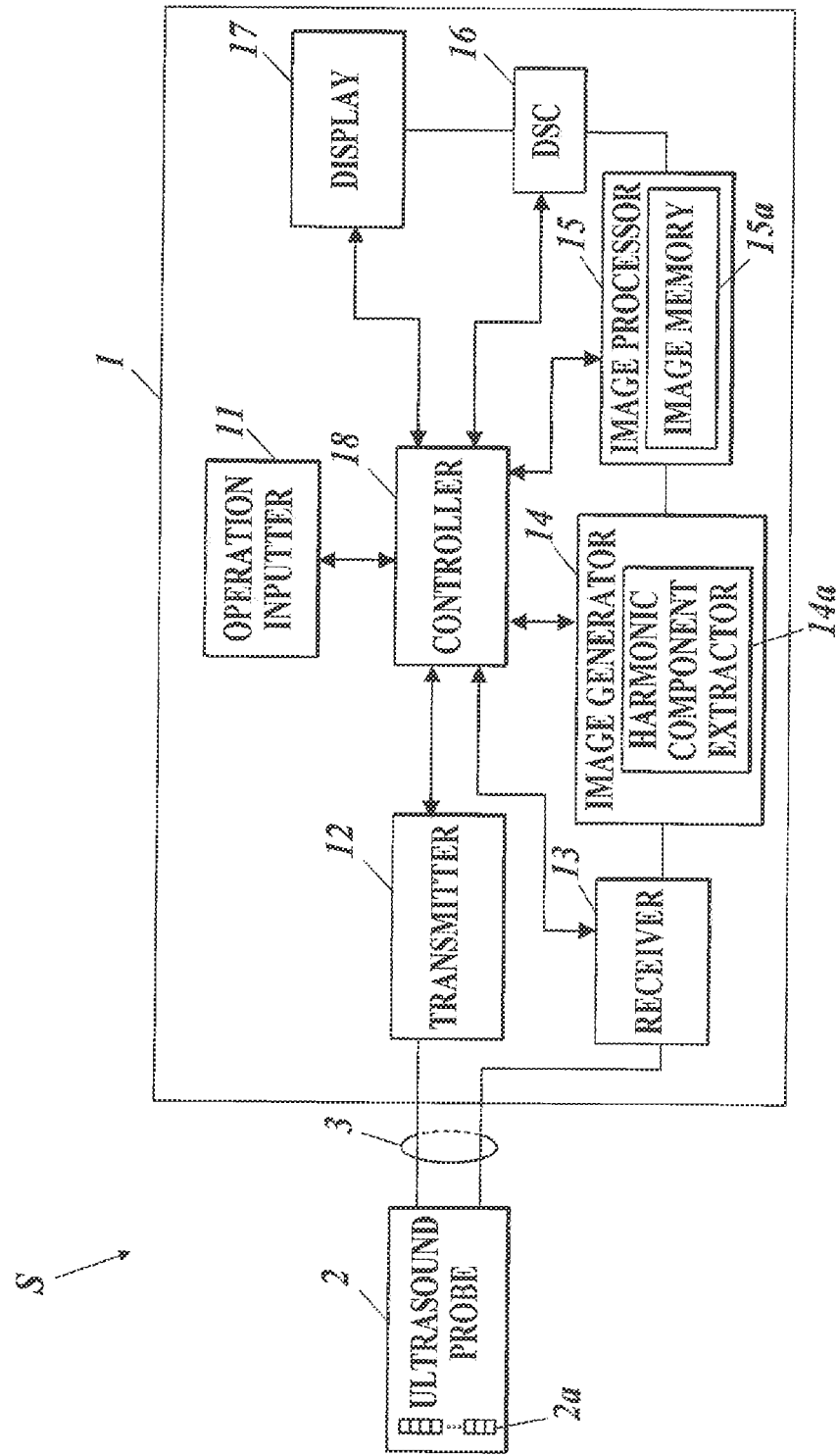
FIG. 2 is a block diagram illustrating a functional configuration of the ultrasound image diagnostic apparatus.
Figure 3:
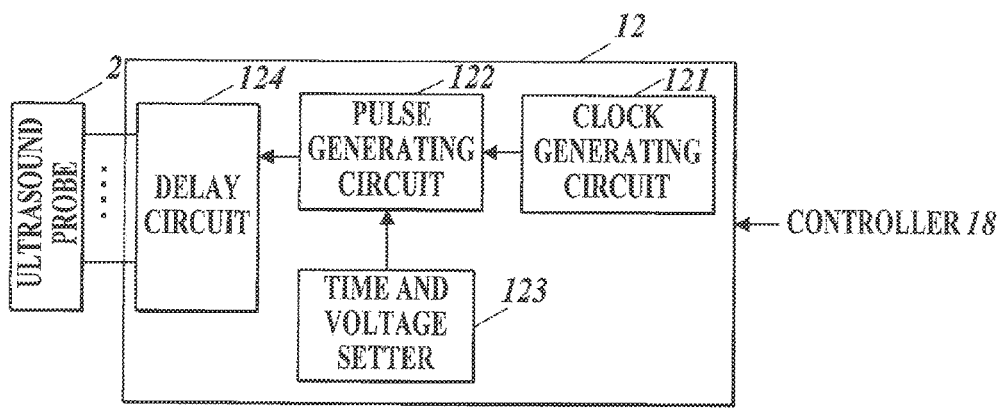
FIG. 3 is a block diagram illustrating a functional configuration of a transmitter.

With reference to FIGS. 1 to 3, an ultrasound image diagnostic apparatus S according to this embodiment will now be described. FIG. 1 is an external view of an ultrasound image diagnostic apparatus S according to an embodiment of the present invention. FIG. 2 is a block diagram illustrating a functional configuration of the ultrasound image diagnostic apparatus S. FIG. 3 is a block diagram illustrating a functional configuration of a transmitter 12.

With reference to FIGS. 1 and 2, an ultrasound image diagnostic apparatus S according to this embodiment includes a body 1 and an ultrasound probe 2. The ultrasound probe 2 transmits ultrasound (transmitted ultrasound) to a subject, such as a living body (not shown), and receives ultrasound reflected on the subject (reflected ultrasound: echo). The body 1 is connected to the ultrasound probe 2 via a cable 3. The body 1 transmits an electric excitation signal to the ultrasound probe 2. In response to the excitation signal, the ultrasound probe 2 transmits ultrasound to the subject, receives ultrasound reflected from the subject, generates an electric reception signal and transmits the generated signal to the body 1. In response to the reception signal from the ultrasound probe 2, the body 1 creates an ultrasound image from the ultrasound image data representing the internal state of the subject.

The ultrasound probe 2 includes transducers 2a composed of piezoelectric elements and an acoustic lens that converges ultrasound beams to the focal point. Multiple transducers 2a are disposed in a one-dimensional array, for example, in an azimuth direction. The ultrasound probe 2 according to this embodiment includes 192 transducers 2a. Alternatively, the transducers 2a may be disposed in a two-dimensional array. Any number of transducers 2a may be used. The ultrasound probe 2 according to this embodiment is an electronic scanning probe of linear scanning type. Alternatively, any type of electronic scanning probe, such as electronic scanning-type, mechanical scanning-type, linear scanning type, sector scanning type, or convex type, may be used.

With reference to FIG. 2, the body 1 includes, for example, an operation inputter 11, a transmitter 12, a receiver 13, an image generator 14, an image processor 15, a digital scan converter (DSC) 16, a display 17, and a controller 18.

The operation inputter 11 includes, for example, switches, buttons, a track ball, a mouse, and a keyboard for entering a diagnosis start command or data, such as personal information of subjects, and outputs operation signals to the controller 18.

The transmitter 12 is a circuit to transmit an electric excitation signal to the ultrasound probe 2 via the cable 3 in accordance with the control of the controller 18 to instruct the ultrasound probe 2 to generate ultrasound. With reference to FIG. 3, the transmitter 12 includes, for example, a clock generating circuit 121, a pulse generating circuit 122, a time and voltage setter 123, and a delay circuit 124.

The clock generating circuit 121 generates clock signals that determine the transmission timing or frequency of an excitation signal. The pulse generating circuit 122 is a circuit that generates pulsed excitation signals at certain intervals. The pulse generating circuit 122 can generate square-wave excitation signals by changing the level of voltage, for example, between three levels (+HV/0 (GND)/−HV) or between five levels (+HV/+MV/0 (GND)/−MV/−HV). The apparatus according to this embodiment has the same negative and positive amplitudes of pulsed signals. Alternatively, different negative and positive amplitudes may be used. The apparatus according to this embodiment changes the voltage between three or five levels before outputting an excitation signal. Alternatively, any number of levels of voltage may be used. However, five levels or less are preferred since it enhances the degree of freedom for controlling frequency components at a low cost and can acquire high-resolution ultrasound.

The time and voltage setter 123 determines the duration and voltage level of each part at the same voltage in excitation signals output from the pulse generating circuit 122. In other words, the pulse generating circuit 122 outputs a pulse-waveform excitation signal in accordance with the duration and the voltage level for each part determined by the time and voltage setter 123. The duration and the voltage level for each part determined by the time and voltage setter 123 may be modified, for example, through input operations at the operation inputter 11.

The delay circuit 124 determines the delay time for transmission timing of an excitation signal for each line path corresponding to each transducer and delays the transmission of excitation signals by the determined delay time to converge ultrasound beams.

The transmitter 12, which has the above-mentioned configuration, shifts multiple transducers 2a through which excitation signals are fed by a predetermined number of transducers 2a for the transmission or reception of ultrasound signals in accordance with the directions of the controller 18 and feeds excitation signals to the selected transducers 2a. Thus the transmitter 12 performs scanning.

In this embodiment, the pulse inversion technique may be used to extract harmonic components described below. In the pulse inversion technique, the transmitter 12 may transmit a first pulse signal and then a second pulse signal having a reverse polarity to the polarity of the first pulse signal on the same scanning lines after a certain time interval. Alternatively, at least one part of excitation period of the first pulse signal may be made to be different in order to send the second pulse signal having a reverse polarity. Alternatively, the second pulse signal may be time-reversed with respect to the first pulse signal.

The receiver 13 is a circuit that receives electric signals from the ultrasound probe 2 via the cable 3 in accordance with the directions of the controller 18. For example, the receiver 13 is provided with an amplifier, an A/D conversion circuit, and a phasing adding circuit. The amplifier amplifies a reception signal at a predetermined amplification factor for each line path corresponding to each transducer 2a. The A/D conversion circuit converts the amplified reception signal into a digital signal (A/D conversion). The phasing adding circuit provides a delay time to the A/D converted reception signal for each line path corresponding to each transducer 2a, adjusts the time phase, and adds (phase-adds) the reception signals to generate sound ray data.

The image generator 14 performs envelope detection or logarithmic amplification on the sound ray data from the receiver 13, adjusts gain, and converts brightness to generate B-mode image data. The B-mode image data indicates the intensity of a reception signal in the form of brightness. The B-mode image data generated at the image generator 14 is sent to the image processor 15. The image generator 14 is provided with a harmonic component extractor 14a.

The harmonic component extractor 14a extracts harmonic components from a reception signal output from the receiver 13 by the pulse inversion technique. The harmonic component extractor 14a according to this embodiment can extract second harmonic components. The method for extracting the second harmonic components is as follows: The above-mentioned first pulse signal and the second pulse signal each generate one ultrasound; the two ultrasounds each generates one reflection ultrasound; the two reflection ultrasounds each generates one reception signal; the two reception signals are synthesized; fundamental frequency components are removed from the synthesized reception signal; and then the synthesized reception signal is filtered, as needed.

The image processor 15 includes an image memory 15a. The image memory 15a is a semiconductor memory, such as a dynamic random access memory (DRAM). The image processor 15 stores B-mode image data output from the image generator 14 in unit of frames in the image memory 15a. Image data in unit of frames is referred to as ultrasound image data or frame image data. The image processor 15 reads the ultrasound image data from the image memory 15a and outputs the ultrasound image data to the DSC 16.

The DSC 16 converts ultrasound image data received from the image processor 15 into image signals by a television signal scanning technique and outputs the image signals to the display 17.

The display 17 may be a liquid crystal display (LCD), cathode-ray tube (CRT) display, organic electroluminescent (EL) display, non-organic electroluminescent (EL) display, or plasma display. The display 17 displays ultrasound images in accordance with image signals output from the DSC 16 on the display screen.

The controller 18 includes, for example, a central processing unit (CPU), a read only memory (ROM) and a random access memory (RAM)). The controller 18 reads various processing programs stored on ROM, including a system program, deploys them on RAM, and intensively controls the operations of the ultrasound image diagnostic apparatus S in accordance with the deployed programs. ROM is composed of a semiconductor memory, such as a non-volatile memory, and contains a system program to operate the ultrasound image diagnostic apparatus S, various processing programs executable on the system program, and data. These programs are stored in the form of program codes that can be read by the computer. CPU performs operations in accordance with the program codes. The RAM provides a work area for temporarily storing various programs executed by the CPU and their data.

Figure 4A:
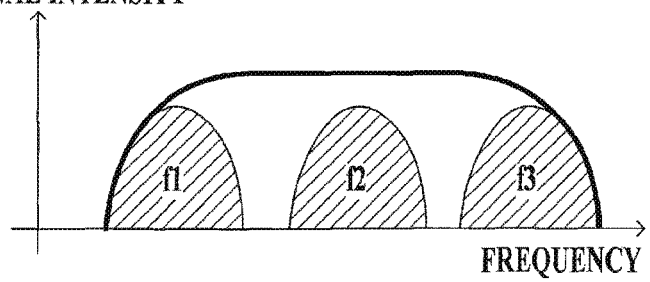
FIG. 4A is a graphical representation of frequency characteristics of the signal intensity of an exemplary ultrasound according to the embodiment.
Figure 4B:
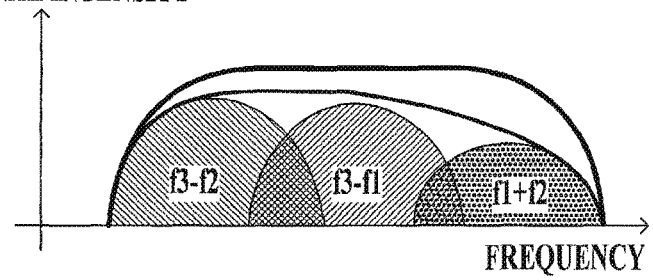
FIG. 4B is a graphical representation of frequency characteristics of the signal intensity of ultrasound reflected from a shallow site.
Figure 4C:
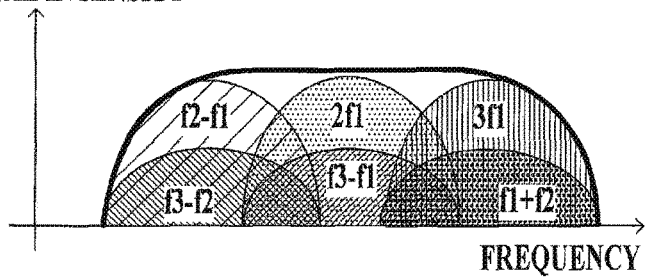
FIG. 4C is a graphical representation of frequency characteristics of the signal intensity of ultrasound reflected from the focal point and its vicinity.
Figure 4D:
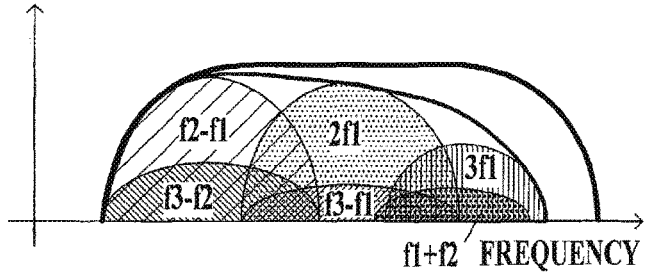
FIG. 4D is a graphical representation of frequency characteristics of the signal intensity of ultrasound reflected from a site deeper than the focal point.
Figure 5:
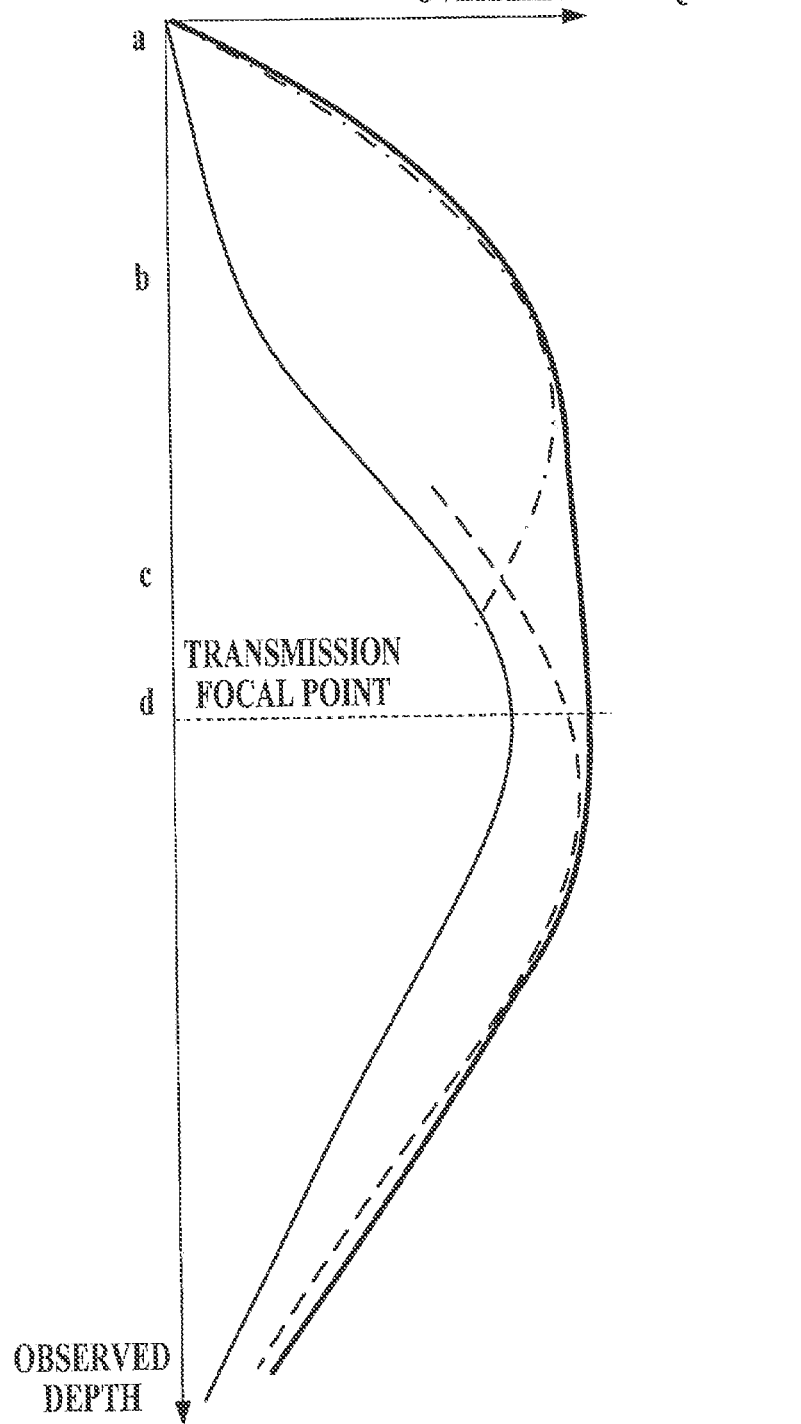
FIG. 5 is a graphical representation of a relation between observed depth and overall image quality according to the embodiment and a conventional technique.
Figure 6A:
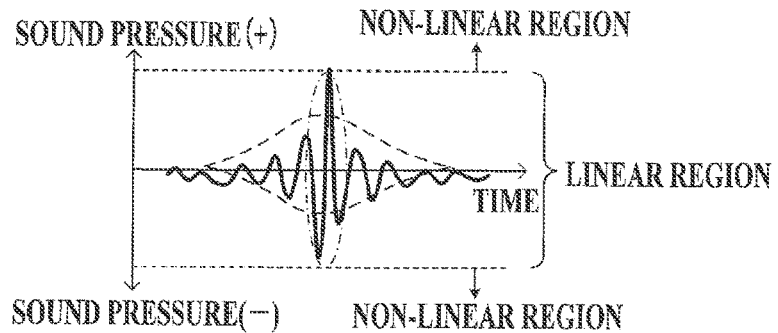
FIG. 6A illustrates a temporal waveform of transmitted ultrasound immediately after transmission.
Figure 6B:
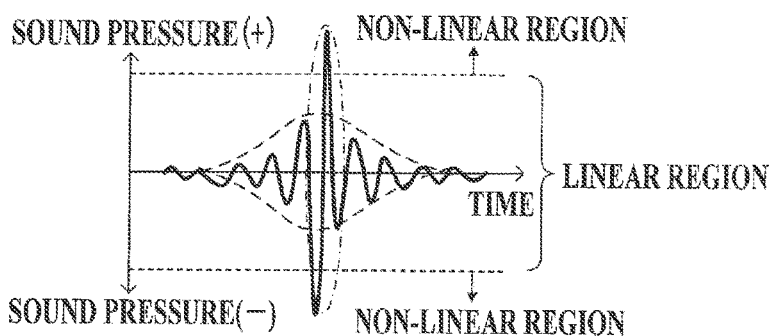
FIG. 6B illustrate a temporal waveform of transmitted ultrasound in a shallow site.
Figure 6C:
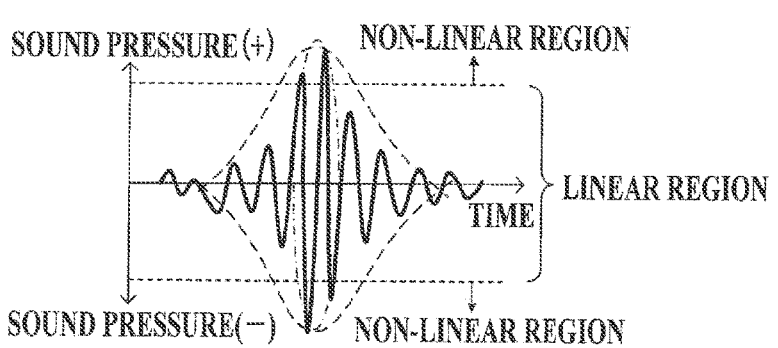
FIG. 6C illustrates a temporal waveform of transmitted ultrasound from a shallow site to the focal point.
Figure 6D:
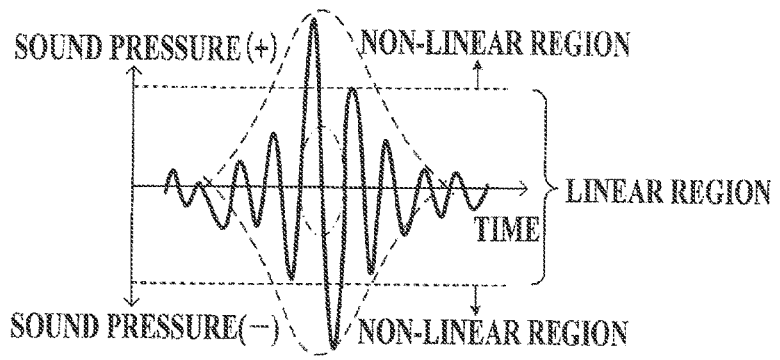
FIG. 6D illustrates a temporal waveform of transmitted ultrasound at or near the focal point.

With reference to FIGS. 4A to 6D, methods for generating an excitation signal and for transmitting and receiving an ultrasound to generate ultrasound image data according this embodiment will now be described. FIG. 4A is a graphical representation of frequency characteristics of the signal intensity of an exemplary ultrasound according to the embodiment; FIG. 4B is a graphical representation of frequency characteristics of the signal intensity of ultrasound reflected from a shallow site; FIG. 4C is a graphical representation of frequency characteristics of the signal intensity of ultrasound reflected from the focal point and its vicinity; and FIG. 4D is a graphical representation of frequency characteristics of the signal intensity of ultrasound reflected from a site deeper than the focal point. FIG. 5 is a graphical representation of a relation between the observed depth and overall image quality according to the embodiment and a conventional technique. FIG. 6A illustrates a temporal waveform of transmitted ultrasound immediately after transmission; FIG. 6B illustrate a temporal waveform of transmitted ultrasound in a shallow site; FIG. 6C illustrates a temporal waveform of transmitted ultrasound from a shallow site to the focal point; and FIG. 6D illustrates a temporal waveform of transmitted ultrasound at or near the focal point.

The ultrasound image diagnostic apparatus according to this embodiment fully utilizes the bandwidth of the ultrasound probe 2 to transmit a wideband ultrasound and controls the distribution of frequency components of an excitation signal waveform and an ultrasound waveform. These functions allow the apparatus to create a high-resolution harmonic image having a high signal-to-noise ratio for shallow sites of a subject and suppress a significant reduction in resolution for deep sites to create a highly uniform harmonic image from shallow to deep sites, without use of a pulse compression technique, despite a long excitation time equivalent to or more than the length of 1.5 waveforms at the lower limit frequency of the −20 dB bandwidth of ultrasound probe.

More specifically, the apparatus transmits an ultrasound signal composed of various frequency components: deep-reaching low-frequency components having a large temporal expanse and high frequency components having a small temporal expanse, as shown in FIGS. 6A to 6D.

Harmonic components used in the tissue harmonic imaging are generated by a nonlinear propagation, which is caused by an increase in sound pressure due to the convergence of ultrasounds. In use of a general ultrasound probe 2 that includes an acoustic lens, ultrasounds are converged in the short axis direction by ultrasound refraction of the acoustic lens and in the long axis direction by transmission delay due to electronic focus. The harmonic generation is controlled based on the dependency of the convergence of ultrasounds on frequency.

Let the apparatus have a configuration that transmits ultrasound containing fundamental frequencies f1, f2, and f3, as shown in FIG. 4A. FIG. 4A shows frequency on the X axis, sensitivity (signal intensity) on the Y axis, and frequency components (transmission and reception frequency band) of the ultrasound probe with the bold solid line. FIGS. 4B to 4D shows frequency on the X axis, signal intensity on the Y axis, a frequency component acquired by combining the frequency components of a reflection ultrasound with the solid line, and the frequency components (transmission and reception frequency band) of the ultrasound probe 2 with the bold solid line.

The converging width of an ultrasound beam is proportional to the inverse of frequency in accordance with the Huygens' principle. In the case where ultrasound has frequency components, as shown in FIG. 4A, the components of the fundamental frequency f3, which has three times the fundamental frequency f1, converge into a one-third beam width. In other words, since the components of the fundamental frequency f3 converge at a density three times that of the fundamental frequency f1, the region containing the components of the fundamental frequency f3 can readily raise sound pressure in response to convergence by the acoustic lens to reach a non-linear region, which generates harmonics.

FIGS. 6A to 6D show time on the X axis and sound pressure on the Y axis. Apart of the temporal waveform mainly containing components of the fundamental frequency f1 or f2 of ultrasound is indicated with the dashed line. A part of the temporal waveform mainly containing components of the fundamental frequency f3 is indicated with the dot-and-dash line. A region with a sound pressure level higher than a positive threshold or lower than a negative threshold represents a non-linear region, while a region with a sound pressure equal to or lower than the positive threshold or equal to or higher than the negative threshold represents a linear region. The observed depth "a" in FIG. 5 corresponds to the depth in FIG. 6A; the observed depth "b" in FIG. 5 corresponds to the depth in FIG. 6B; the observed depth "c" in FIG. 5 corresponds to the depth in FIG. 6C; and the observed depth "d" in FIG. 5 corresponds to the depth in FIG. 6D.

Immediately after the transmission of an ultrasound from the ultrasound probe 2, as shown in FIG. 6A, fundamental frequency components are within the linear region and high-frequency components, localized, as shown with the dot-and-dash line, generate a high sound pressure. For the transmission of an ultrasound to a shallow site of a subject (convergence by the acoustic lens), as shown in FIG. 6B, a region mainly containing highly converging components of the high fundamental frequency f3 reaches the non-linear region due to convergence by the acoustic lens to generate harmonics due to differences in propagating speed. For shallow sites, i.e., near-surface sites, broadband harmonic components, mainly composed of f3 subharmonics (differential harmonics), as shown in FIG. 4B, are generated by acoustic lens even with the electronic focal point in a deep site. Ultrasound that reaches the non-linear region through convergence is limited to part of a waveform containing harmonic components. In other words, only a limited part of a long pulse reaches the non-linear region, which generates harmonics, to enable a high-resolution image to be produced. For harmonic components reflected and received after generation at a shallow site immediately after the transmission, the components of the fundamental frequency f3 have greater signal intensity than the components of the fundamental frequency f1 or f2, as shown in FIG. 4B.

In the intermediate region between a shallow site and the long-axis focal point, as shown in FIG. 6C, the generation of harmonics composed of the fundamental frequency f3 at the shallow site and the generation of those composed of the fundamental frequency f1 or f2 near the focal point are mutually complementary.

At or near the focal point, as shown in FIG. 6D, a part of the temporal waveform mainly containing high frequency components at the fundamental frequency f3 has sound pressure reduced to that of the linear region due to attenuation and energy transition to harmonic components. In contrast, at a shallow site, which is less affected by attenuation, the sound pressure of low-frequency components of the fundamental frequency f1 or f2, which was within the linear region, reaches the non-linear region due to electronic focus, which leads to the generation of harmonic components. Similar to the shallow site, only a limited part of a long pulse reaches the non-linear region, which generates harmonics, to achieve a high resolution. As shown in FIG. 4C, at and near the focal point, newly generated harmonics are mainly composed of the fundamental frequency f1 or f2 and substantially no harmonics composed of the fundamental frequency f3 are generated. Since the signal strength at and near the focal point is more attenuated than the shallow site, the harmonic reflected and received has the signal intensity as shown in the drawings. The 3f1 components, that is, the third harmonic components, shown in the drawings, are extracted through subtraction and band-passing, unlike other components, which are extracted through addition in pulse inversion, phase-adjusted, as needed, and added to a sound-ray signal for other harmonic components. The 3f1 components may be phase-adjusted using an all-pass filter to combine with other harmonic components in accordance with a waveform superimpose principle to acquire broadband reception signals. At a site deeper than the focal point, as shown in FIG. 4D, where generation of harmonics prevails over attenuation, harmonic components that can be reflected and received gradually decrease. Harmonic components of the fundamental frequency f1 or f2 do not rapidly decrease because harmonic generation continues for a certain time, while harmonic components of the fundamental frequency f3 significantly decrease because they are affected only by attenuation. Thus, harmonic components of the fundamental frequency f3 account for a fairly small percentage of the harmonic components reflected and received.

With reference to FIG. 5, the overall image quality corresponding to the observed depth of the ultrasound shown in FIG. 4A is better than that of a conventional technique for acquiring a harmonic image that involves the use of a low-frequency fundamental waveform of an ultrasound probe, as later described in Comparative Example 1. The overall image quality includes a signal-to-noise ratio and resolution of an ultrasound image created from generated image data. FIG. 5 indicates the harmonic components of the fundamental frequency f3 generated in the first generating process with the dashed line; harmonic components of the fundamental frequency f1 or f2 generated in the second generating process with the dot-and-dash line; the overall image quality of the harmonic components acquired by combining the harmonic components generated in the first and second generating processes according to this embodiment with the bold solid line; and the overall image quality of a conventional example with the medium line. In the conventional example, sound pressure cannot be boosted to a satisfactory level at a shallow site due to the low frequency of ultrasound and thus satisfactory harmonic signals cannot be acquired, which precludes the improvement of image quality. In contrast, the multi-step harmonic generation utilizing a difference in convergence characteristics allows high-resolution ultrasound images having a high signal-to-noise ratio to be acquired in a wide range from shallow to near-focal point sites.

The waveform of ultrasound is shown in FIG. 4A for illustrative purpose and any other waveforms may also be used. The prerequisite for the multi-step harmonic generation is as follows: Higher frequency components of ultrasound have a smaller temporal expanse, while lower frequency components have a larger temporal expanse.

Figure 8:
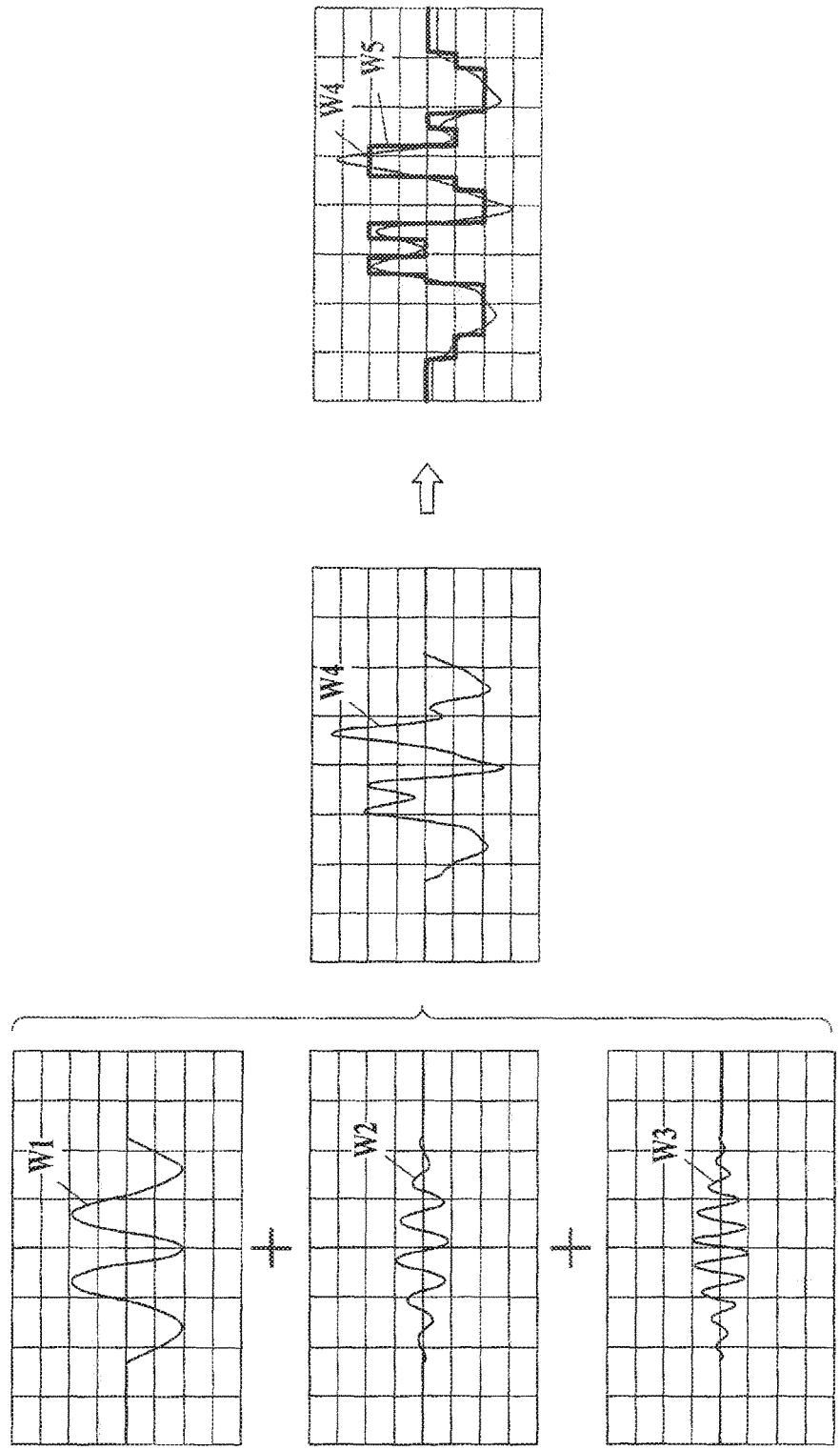
FIG. 8 illustrates the generation of a temporal waveform of an excitation signal in Example 5 by waveform synthesis according to the embodiment.

With reference to FIGS. 7A to 10C, methods for generating the above-mentioned ultrasound waveform will now be described. With reference to FIGS. 7A to 8, a first method for generating the ultrasound waveform will now be described. FIG. 7A illustrates traditional waveform synthesis. FIG. 7B illustrates waveform synthesis according to this embodiment. FIG. 8 illustrates a method for generating a temporal waveform of an excitation signal in Example 5 described below by waveform synthesis according to this embodiment.

In the first method for generating the ultrasound waveform, the transmitter 12 (pulse generating circuit 122) modulates and synthesizes multiple temporal waveforms (pluses), each having a different frequency, to generate an excitation signal waveform. In contrast, the traditional waveform synthesis, as shown in FIG. 7A, involves filtering and a simple synthesis of multiple (three) waveforms, each having a different frequency, to generate an excitation signal. More specifically, the filtering is performed with rectangular windows having the same time width, as indicated with the dotted line. In the traditional waveform synthesis, a excitation time equivalent to or more than the length of 1.5 waveforms at the lower limit frequency of the −6 dB transmission bandwidth precludes the generation of ultrasound such that high-frequency components have a smaller temporal expanse and low-frequency components have a larger temporal expanse, as shown in FIG. 6A, and thus the multi-step harmonic generation cannot be performed. The waveforms in FIGS. 7A and 7B have time on the x-axis and signal intensity (voltage) on the Y axis.

The modulation method according to this embodiment may be, for example, modulation of the amplitude of a temporal waveform (amplitude modulation (AM) modulation) using the hanning window indicated with the dotted line, as shown in FIG. 7B, frequency modulation (FM), which involves the transition of frequency, or a combination thereof.

In FIG. 7B, the left waveform is a temporal waveform acquired by FM-modulating a predetermined waveform and filtering the FM-modulated waveform with a rectangular window. The middle and right waveforms are temporal waveforms acquired through AM modulation with the hanning windows shown with the dotted lines. The transmitter 12 synthesizes and drives these three waveforms to generate ultrasound, as shown in FIG. 6A. In the synthesis of the waveforms, the amplitude of each of the three waveforms is preferably multiplied by an appropriate multiplying factor. The multiplying factors are selected so as to correct a difference in transmission sensitivity of the ultrasound probes and transmit ultrasound having a desired frequency-intensity ratio.

Besides AM modulation using windows having the same time width, as shown in FIG. 7B, windows having different time widths may be used for AM modulation. In other words, besides gradual changes in amplitude, a rectangular window capable of changing amplitude in an ON/OFF manner may also be used in the apparatus according to this embodiment to control the temporal expanse of each frequency component.

In the example shown in FIG. 7B, the first to third temporal waveforms correspond to the components of the fundamental frequency f1, f2, and f3, respectively, of an excitation signal. Any number of frequency components may be used for synthesis, but at least two, preferably three or more frequencies should be synthesized into an excitation signal waveform to create the above-mentioned ultrasound waveform.

A smaller difference in the frequency of signal components to be synthesized results in a smaller difference in the convergence of the ultrasound beams. The smaller difference in the convergence, in turn, precludes the multi-step harmonic generation, which utilizes the difference in the convergence. Waveforms to be synthesized preferably include components having a frequency at least two times higher than the lowest frequency.

The waveform of an excitation signal acquired by synthesizing multiple frequency components as described above may be used in the transmitter 12, which functions as a waveform transmitter, etc., without any modifications. Alternatively, the number of voltage levels, for example, five levels of voltage, may be assigned to the original waveform of an excitation signal to acquire an approximate waveform so that the transmitter 12 capable of handling a limited number of voltage levels can drive the waveform. In other words, the pulse generating circuit 122 may synthesize AM- or FM-modulated temporal waveforms and then assign the duration and voltage level, for each part, determined by the time and voltage setter 123 to the synthesized waveform to generate an excitation signal, provide the generated excitation signal with delay determined by the delay circuit 124, and output the resulting excitation signal to the ultrasound probe 2. Alternatively, pre-assigned waveform information may be stored in the memory (not shown) to generate an excitation signal based on the information. The latter method is preferred because it does not complicate the apparatus. A waveform transmitter capable of transmitting any waveforms is preferred for detailed adjustment of driving control, but five levels of voltage are preferred from the perspective of practical and satisfactory driving control and cost reduction of the apparatus.

Figure 34A:
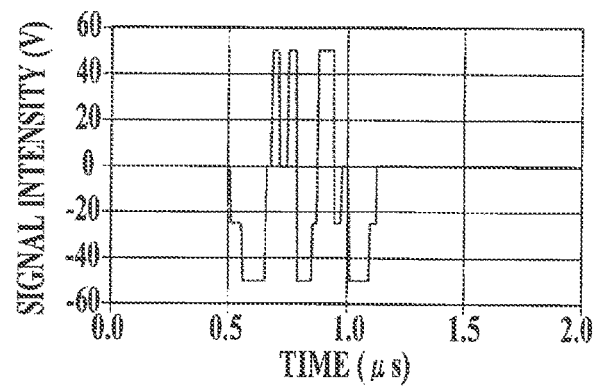
FIG. 34A is a graphical representation of a temporal change in the signal intensity of an excitation signal in Example 4.
Figure 34B:
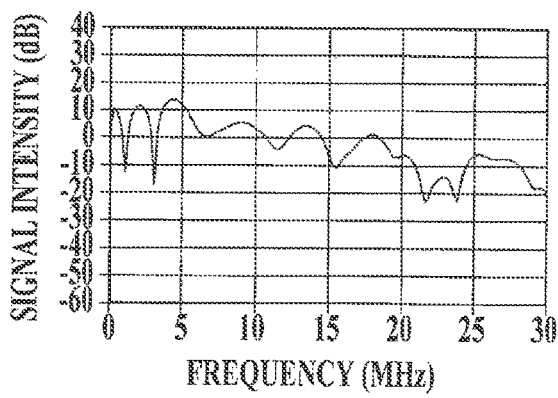
FIG. 34B illustrates the power spectrum of the excitation signal in Example 4.

A specific method for assigning each voltage level to a synthesized waveform will now be described using excitation signal waveform no. 12 in Example 5 described below. The excitation signal waveform no. 12 in Example 5 is an excitation signal having a temporal change in the signal intensity of an excitation signal, as shown in FIG. 34A and having frequency characteristics of the signal intensity, as shown in FIG. 34B.

With reference to FIG. 8, three waveforms W1, W2, and W3 modulated as shown in FIG. 7B are generated; the amplitude of the waveform W1 is doubled, while the amplitudes of the waveforms W2 and W3 being retained; and these waveforms are synthesized into a waveform W4. A bias (DC component) is added to the synthesized waveform in the amplitude direction that does not affect transmission, in consideration of the balance between positive and negative amplitudes. Five levels are assigned, as shown in FIG. 8, to acquire a waveform W5, which is equivalent to waveform no. 12 of an excitation signal in Example 5.

In case of FM modulation, as shown in the left temporal waveform in FIG. 7B, modulation that involves the transition of frequency in order of low, high, and low is preferred during the duration of a waveform to acquire the above waveform of ultrasound.

Of all the waveforms to be synthesized, the waveform having the lowest frequency components is preferably FM-modulated to increase low-frequency components, while retaining the frequency bandwidth.

Figure 9:
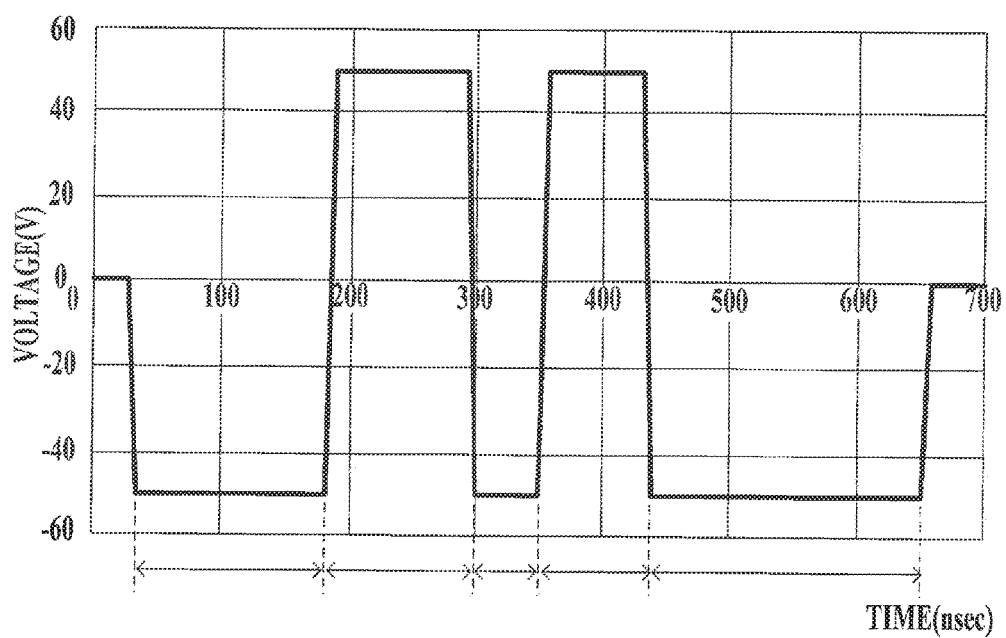
FIG. 9 illustrates parts of an excitation signal.
Figure 10A:
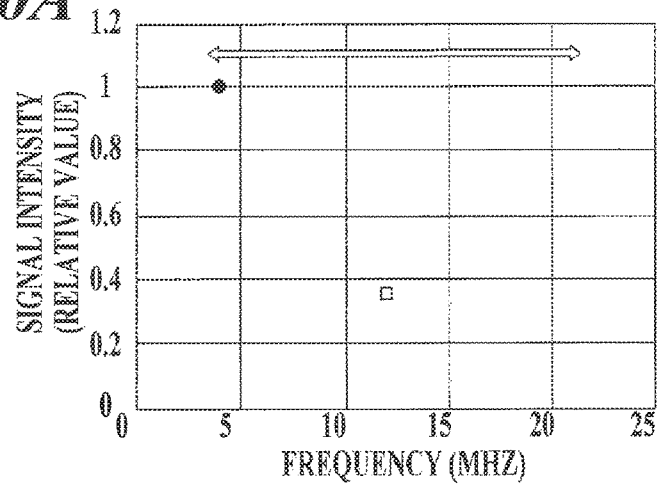
FIG. 10A illustrates a distribution of frequency components into which parts of the excitation signal in Comparative Example 2 are converted.
Figure 10B:
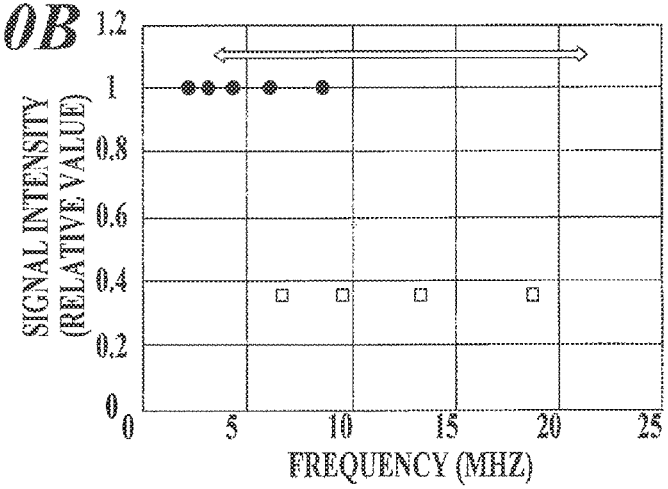
FIG. 10B illustrates a distribution of frequency components into which parts of the excitation signal in Example 2 are converted.
Figure 10C:
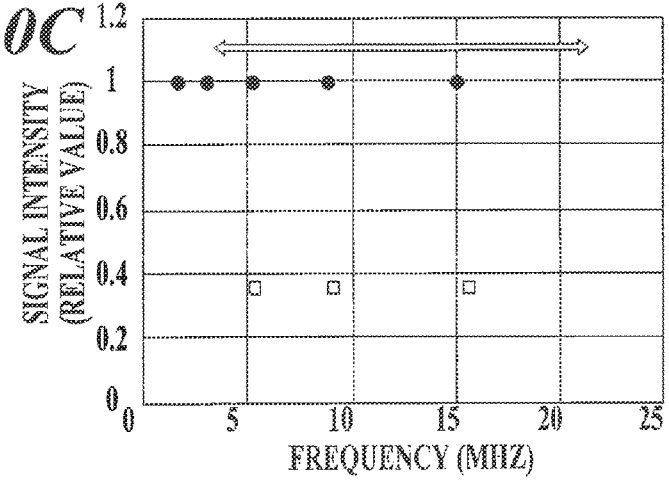
FIG. 10C illustrates a distribution of frequency components into which parts of the excitation signal in Comparative Example 8 are converted.
Figure 11A:
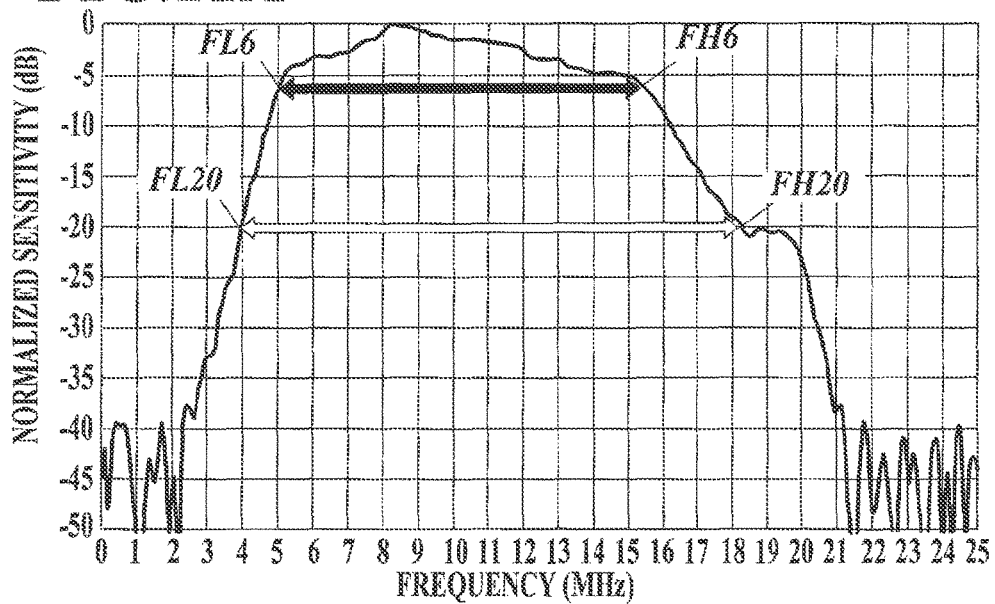
FIG. 11A is a graphical representation of frequency characteristics of the normalized transmission and reception sensitivity of the ultrasound probe.
Figure 11B:
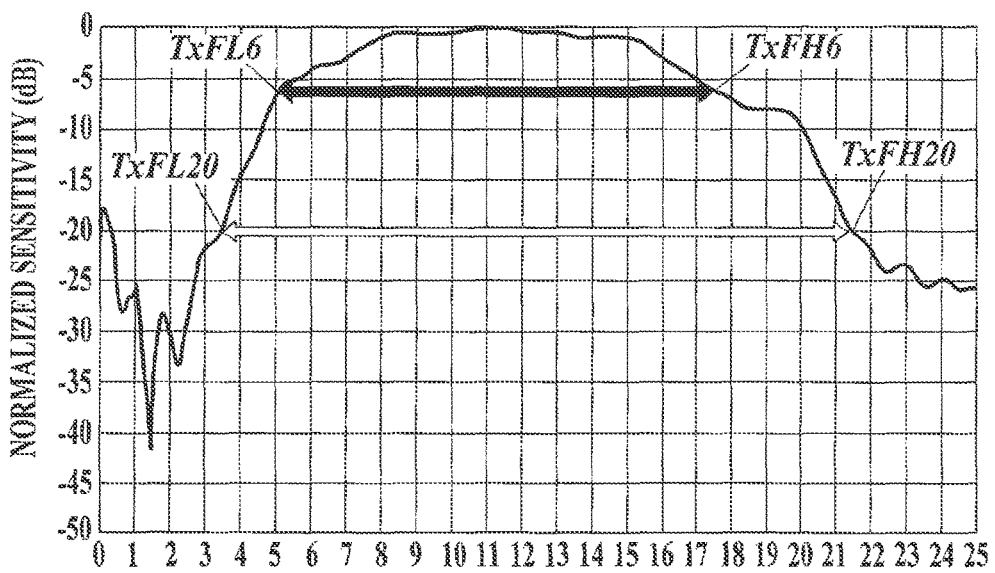
FIG. 11B is a graphical representation of frequency characteristics of the normalized transmission sensitivity of the ultrasound probe.

With reference to FIGS. 9 to 11B, a second method for generating the above-mentioned ultrasound waveform will now be described. FIG. 9 illustrates the parts of an excitation signal. FIG. 10A illustrates a distribution of frequency components into which the parts of the excitation signal in Comparative Example 2, described below, are converted. FIG. 10B illustrates a distribution of frequency components into which the parts of the excitation signal in Example 2, described below, are converted. FIG. 10C illustrates a distribution of frequency components into which the parts of the excitation signal in Comparative Example 8, described below, are converted. FIG. 11A is a graphical representation of frequency characteristics of the normalized transmission and reception sensitivity of the ultrasound probe 2. FIG. 11B is a graphical representation of frequency characteristics of the normalized transmission sensitivity of the ultrasound probe 2.

The second method for generating the above-mentioned ultrasound waveform involves prolongation of the duration of any one part of the excitation signal, as shown in, for example, FIG. 9, to acquire a wide bandwidth. FIG. 9 shows time on the X axis and signal intensity (voltage) on the Y axis. The duration of the voltage levels of the excitation signal waveform represent parts indicated with double-headed arrows. One voltage level is a logical value of the excitation signal, excluding variations in measured voltage due to fluctuation in power supply voltage. The duration of one voltage level represents one part. The duration of parts of the resulting excitation signal is converted into a frequency with the duration of each part regarded as 0.5 waveforms.

Figure 14A:
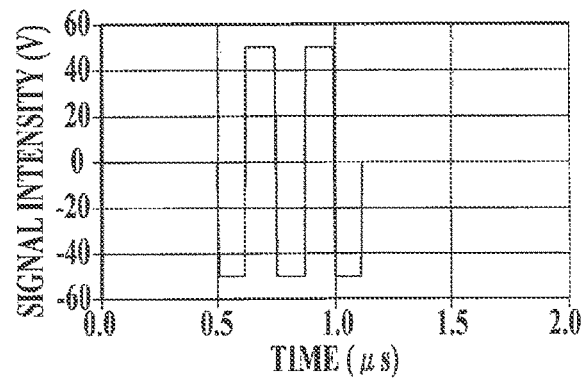
FIG. 14A is a graphical representation of a temporal change in the signal intensity of an excitation signal in Comparative Example 2.
Figure 14B:
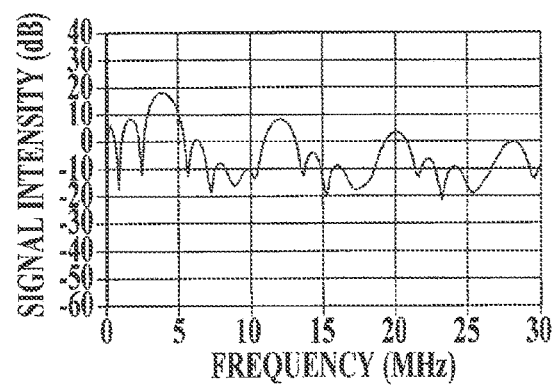
FIG. 14B illustrates the power spectrum of the excitation signal in Comparative Example 2.
Figure 26A:
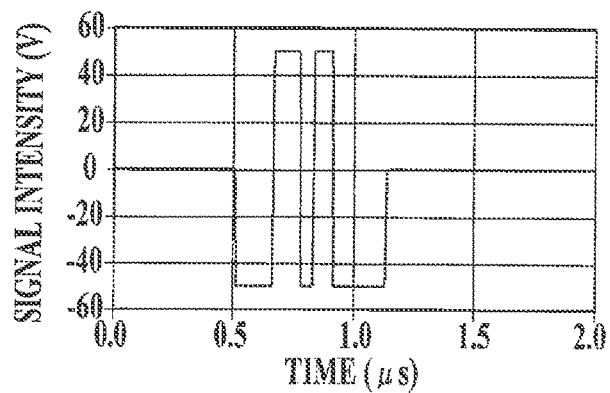
FIG. 26A is a graphical representation of a temporal change in the signal intensity of an excitation signal in Example 2.
Figure 26B:
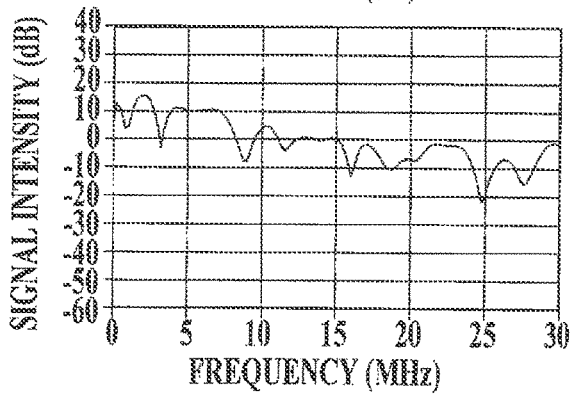
FIG. 26B illustrates the power spectrum of the excitation signal in Example 2.
Figure 30A:
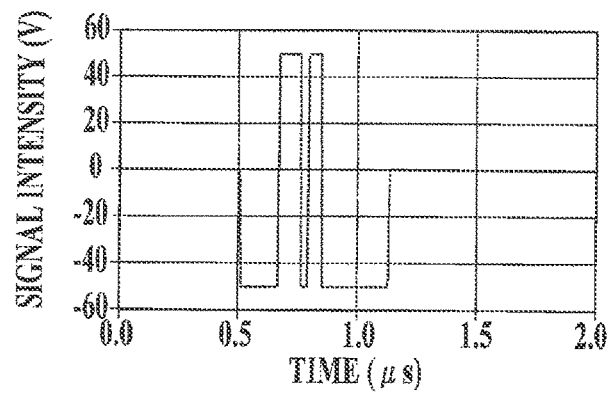
FIG. 30A is a graphical representation of a temporal change in the signal intensity of an excitation signal in Comparative Example 8.
Figure 30B:
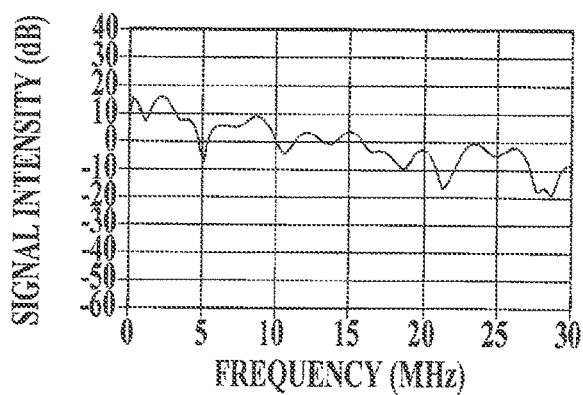
FIG. 30B illustrates the power spectrum of the excitation signal in Comparative Example 8.

The second method will now be described, with excitation signal waveform no. 2 in Comparative Example 2 (described below), excitation signal waveform no. 8 in Example 2 (described below) and excitation signal waveform no. 10 in Comparative Example 8 (described below) taken as examples. The excitation signal waveform 2 in Comparative Example 2 is an excitation signal having a temporal change in the signal intensity, as shown in FIG. 14A, and has frequency characteristics of the signal intensity, as shown in FIG. 14B. The excitation signal waveform 8 in Example 2 is an excitation signal having a temporal change in the signal intensity as shown in FIG. 26A, and having frequency characteristics of the signal intensity as shown in FIG. 26B. The excitation signal waveform 10 in Comparative Example 8 is an excitation signal having a temporal change in the signal intensity as shown in FIG. 30A, and having frequency characteristics of the signal intensity as shown in FIG. 30B.

A (first) frequency component into which parts of the excitation signals in Comparative Example 2, Example 2, and Comparative Example 8 are converted is shown with a black circle (●) in FIGS. 10A to 10C. FIGS. 10A to 10C show frequency [MHz] on the X axis and signal intensity (relative value) on the Y axis. The −20 dB bandwidth for the transmission sensitivity of the ultrasound probe 2 (−20 dB transmission bandwidth) is shown with a double-headed arrow. A third harmonic frequency component of a rectangular wave into which each part is converted is shown with a white square (□).

With reference to FIGS. 11A and 11B, the frequency characteristics of the ultrasound probe 2 will now be described. FIGS. 11A and 11B show frequency [MHz] on the X axis and normalized sensitivity [dB] on the Y axis. The normalized sensitivity has the maximum sensitivity of 0 [dB]. FIG. 11A shows a −6 dB transmission and reception sensitivity bandwidth with the double-headed black arrow and a −20 dB transmission and reception sensitivity bandwidth with the double-headed white arrow. The −6 dB transmission and reception bandwidth has an upper limit frequency of FH6 and a lower limit frequency of FL6. The −20 dB transmission and reception bandwidth has an upper limit frequency of FH20 and a lower limit frequency of FL20. The −6 dB transmission and reception bandwidth of the ultrasound probe 2 has a central frequency of FC6.

FIG. 11B shows the −6 dB transmission sensitivity bandwidth with the double-headed black arrow and the −20 dB transmission sensitivity bandwidth with the double-headed white arrow. The −6 dB transmission bandwidth has an upper limit frequency of TxFH6 and a lower limit frequency of TxFL6. The −20 dB transmission bandwidth has an upper limit frequency of TxFH20 and a lower limit frequency of TxFL20. FIGS. 10A to 10C show the −20 dB transmission bandwidth of the ultrasound probe 2 shown in FIG. 11B.

A waveform with a constant excitation time repeated, like the waveform 2 in Comparative Example 2, has frequency components only in part of the −20 dB transmission bandwidth of the ultrasound probe 2 as shown in FIG. 10A, which contains only one third harmonic frequency component of a rectangular wave into which each part is converted. This results in narrow-band ultrasound transmission and thus precludes the acquisition of broadband harmonic components. In contrast, the prolongation of the duration of each part to make irregular driving pulses, like the waveform 8 in Example 2, results in an even distribution of frequency components of an excitation signal in the −20 dB transmission bandwidth of the ultrasound probe 2 as shown in FIG. 10B. This enhances the band flatness and leads to the acquisition of broadband harmonic components from these frequency components. An increase in the duration of parts near the center and a decrease in the duration of parts near the ends allows the temporal expanse of each frequency component in the temporal waveform to be controlled and thus enables the multi-step harmonic generation.

An excessive prolongation of the duration of each part, like the waveform 10 in Comparative Example 8, decreases the relative number of low-frequency components that significantly contribute to the generation of deep-site harmonics and thus reduces the penetration, as shown in FIG. 10C, which is contrary to the object of the present invention. The degree of prolongation is preferably such that a normalized frequency obtained as follows has a standard deviation of 0.1-0.3: The duration of parts of the excitation signal is converted into a frequency with the duration of each part regarded as 0.5 waveforms and the converted frequency is normalized with respect to the central frequency FC6 of the −6 dB transmission and reception bandwidth of the ultrasound probe 2. For example, the duration of parts of 125 [nsec] can be converted into a frequency of 4 [MHz] with each part regarded as 0.5 waveforms. The frequency of 4 [MHz] is normalized into 0.39 with respect to the central frequency FC6, which is 10.25 [MHz], of the −6 dB transmission and reception bandwidth.

A frequency into which parts are converted with each part regarded as 0.5 waveforms preferably ranges from ⅓ of the lower limit frequency (TxFL20) of the −20 dB transmission bandwidth of the ultrasound probe 2 to the upper limit frequency (TxFH20) of the −20 dB transmission bandwidth of the ultrasound probe 2. A frequency lower than ⅓ the lower limit frequency (TxFL20) results in the first frequency components and the third harmonic components, which are inevitably involved because of a square wave, having a frequency lower than the frequency TxFL20, which no longer contribute to the transmission of ultrasound. Similarly, the converted frequency higher than the frequency of TxFH20 also results in the first frequency components and the third harmonic components having a frequency higher than the frequency TxFH20, which no longer contribute to the transmission of ultrasound.

With reference to FIGS. 11A to 41B, specific examples of the ultrasound probe 2 and Examples and Comparative Examples of excitation signals and ultrasound will now be described. First, the specific examples of the ultrasound probe 2 will be described with reference to FIGS. 11A and 11B.

In generation of excitation signals and ultrasound in the following Examples and Comparative Examples, the ultrasound probe 2 is used which has frequency characteristics of the normalized transmission and reception sensitivity as shown in FIG. 11A, and frequency characteristics of the normalized transmission sensitivity as shown in FIG. 11B. In FIG. 11A, the −20 dB transmission and reception bandwidth ranges from 4.0 to 18.3 [MHz] and the central frequency FC6 of the −6 dB transmission and reception bandwidth is 10.25 [MHz].

In FIG. 11B, the −20 dB transmission bandwidth ranges from 3.4 to 21.3 [MHz] and the frequency TxFL6 is 5.0 [MHz].

With reference to FIGS. 12A to 41B, excitation signals and ultrasound in Examples 1 to 6 and Comparative Examples 1 to 10 will now be described.

Comparative Example 1

Figure 12A:
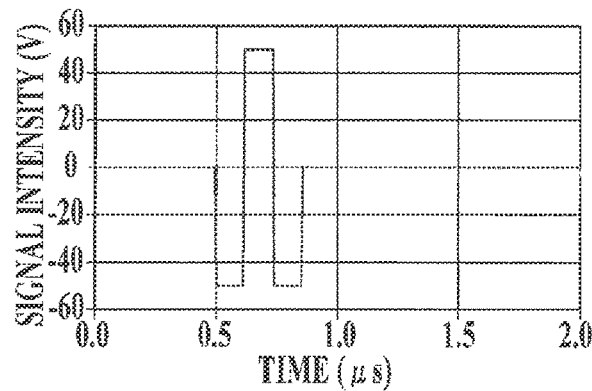
FIG. 12A is a graphical representation of a temporal change in the signal intensity of an excitation signal in Comparative Example 1.
Figure 12B:
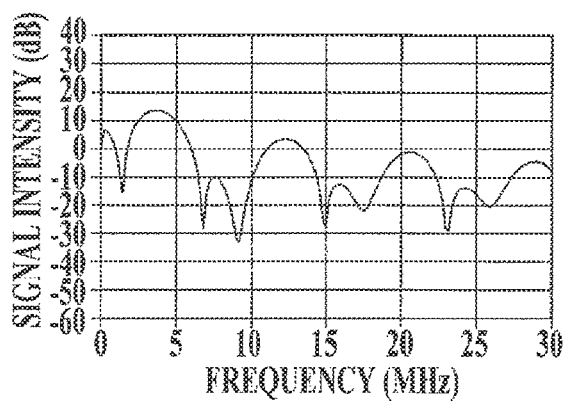
FIG. 12B illustrates the power spectrum of the excitation signal in Comparative Example 1.
Figure 13A:
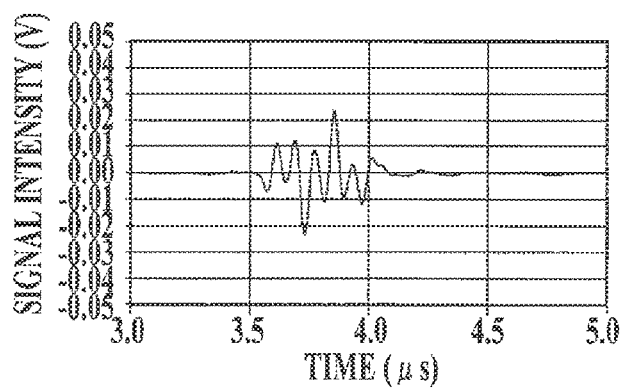
FIG. 13A is a graphical representation of a temporal change in the signal intensity of ultrasound in Comparative Example 1.
Figure 13B:
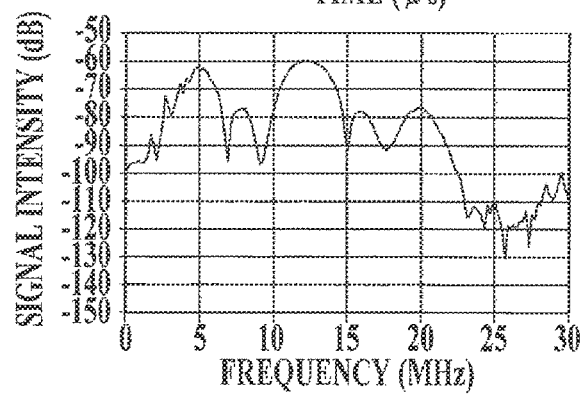
FIG. 13B illustrates the power spectrum of the ultrasound in Comparative Example 1.

The excitation signal waveform in Comparative Example 1 is referred to as waveform 1 (waveform no.: 1). FIG. 12A is a graphical representation of a temporal change in the signal intensity of an excitation signal in Comparative Example 1. FIG. 12B illustrates the power spectrum of the excitation signal in Comparative Example 1. FIG. 13A is a graphical representation of a temporal change in the signal intensity of ultrasound in Comparative Example 1. FIG. 13B illustrates the power spectrum of the ultrasound in Comparative Example 1.

The waveform of the excitation signal in Comparative Example 1 generated by the transmitter 12 has a temporal change in the signal intensity as shown in FIG. 12A. The power spectrum obtained by Fourier transform of the excitation signal shown in FIG. 12A has frequency characteristics of the signal intensity as shown in FIG. 12B. The waveform of ultrasound transmitted in response to the excitation signal in FIG. 12A which is fed to the ultrasound probe 2 has a temporal change in the signal intensity as shown in FIG. 13A. The power spectrum obtained by Fourier transform of the ultrasound shown in FIG. 13A has frequency characteristics of the signal intensity as shown in FIG. 13B.

FIGS. 12A, 13A to 41A shows time [µS] on the X axis and signal intensity (voltage) [V] on the Y axis. FIGS. 12B, 13B to 41B show frequency [MHz] on the X axis and signal intensity [dB] on the Y axis.

Comparative Example 2

Figure 15A:
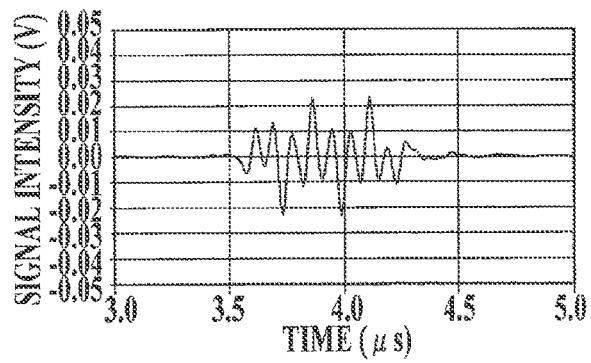
FIG. 15A is a graphical representation of a temporal change in the signal intensity of ultrasound in Comparative Example 2.
Figure 15B:
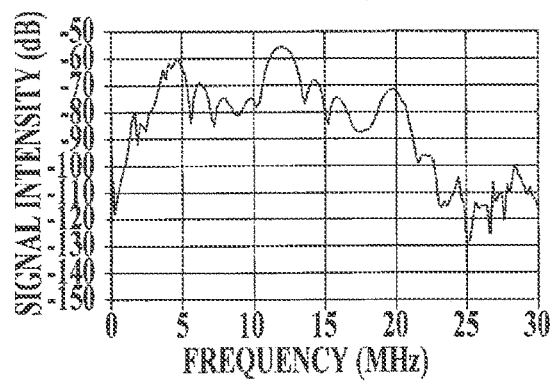
FIG. 15B illustrates the power spectrum of the ultrasound in Comparative Example 2.

The excitation signal waveform in Comparative Example 2 is referred to as waveform 2 (waveform no.: 2). FIG. 14A is a graphical representation of a temporal change in the signal intensity of an excitation signal in Comparative Example 2. FIG. 14B illustrates the power spectrum of the excitation signal in Comparative Example 2. FIG. 15A is a graphical representation of a temporal change in the signal intensity of ultrasound in Comparative Example 2. FIG. 15B illustrates the power spectrum of the ultrasound in Comparative Example 2.

The waveform of the excitation signal in Comparative Example 2 generated by the transmitter 12 has a temporal change in the signal intensity as shown in FIG. 14A. The power spectrum obtained by Fourier transform of the excitation signal shown in FIG. 14A has frequency characteristics of the signal intensity as shown in FIG. 14B. The waveform of ultrasound transmitted in response to the excitation signal in FIG. 14A which is fed to the ultrasound probe 2 has a temporal change in the signal intensity as shown in FIG. 15A. The power spectrum obtained by Fourier transform of the ultrasound shown in FIG. 15A has frequency characteristics of the signal intensity as shown in FIG. 15B.

Comparative Example 3

Figure 16A:
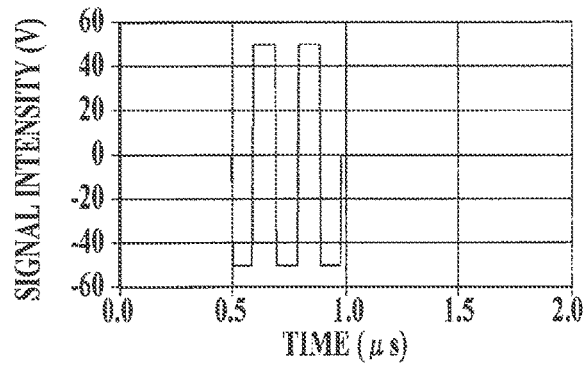
FIG. 16A is a graphical representation of a temporal change in the signal intensity of an excitation signal in Comparative Example 3.
Figure 16B:
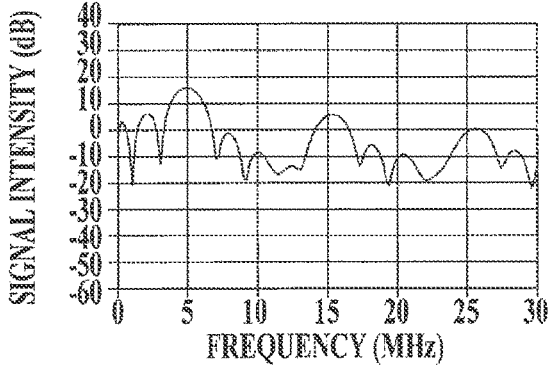
FIG. 16B illustrates the power spectrum of the excitation signal in Comparative Example 3.
Figure 17A:
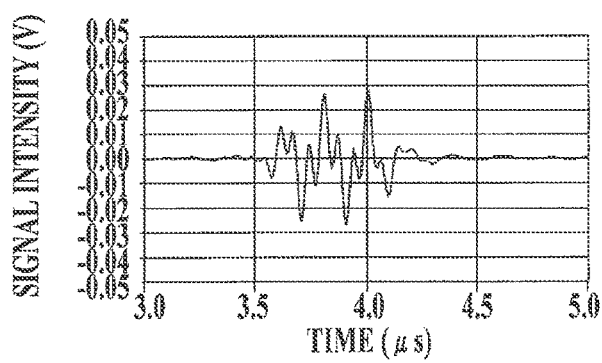
FIG. 17A is a graphical representation of a temporal change in the signal intensity of ultrasound in Comparative Example 3.
Figure 17B:
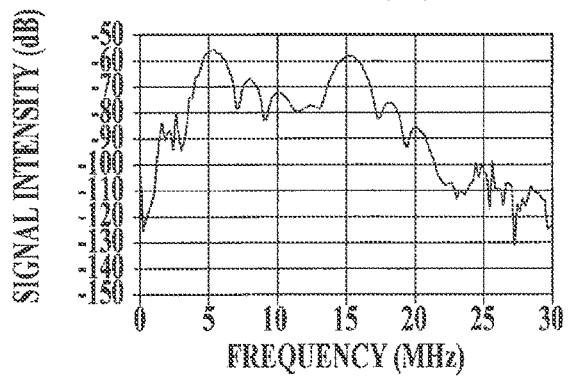
FIG. 17B illustrates the power spectrum of the ultrasound in Comparative Example 3.

The excitation signal waveform in Comparative Example 3 is referred to as waveform 3 (waveform no.: 3). FIG. 16A is a graphical representation of a temporal change in the signal intensity of an excitation signal in Comparative Example 3. FIG. 16B illustrates the power spectrum of the excitation signal in Comparative Example 3. FIG. 17A is a graphical representation of a temporal change in the signal intensity of ultrasound in Comparative Example 3. FIG. 17B illustrates the power spectrum of the ultrasound in Comparative Example 3.

The waveform of the excitation signal in Comparative Example 3 generated by the transmitter 12 has a temporal change in the signal intensity as shown in FIG. 16A. The power spectrum obtained by Fourier transform of the excitation signal shown in FIG. 16A has frequency characteristics of the signal intensity as shown in FIG. 16B. The waveform of ultrasound transmitted in response to the excitation signal in FIG. 16A which is fed to the ultrasound probe 2 has a temporal change in the signal intensity as shown in FIG. 17A. The power spectrum obtained by Fourier transform of the ultrasound shown in FIG. 17A has frequency characteristics of the signal intensity as shown in FIG. 17B.

Comparative Example 4

Figure 18A:
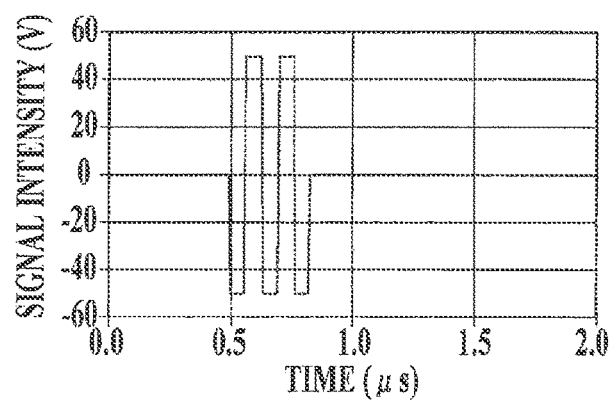
FIG. 18A is a graphical representation of a temporal change in the signal intensity of an excitation signal in Comparative Example 4.
Figure 18B:
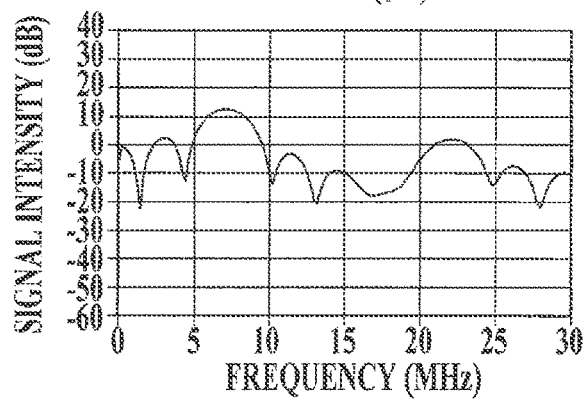
FIG. 18B illustrates the power spectrum of the excitation signal in Comparative Example 4.
Figure 19A:
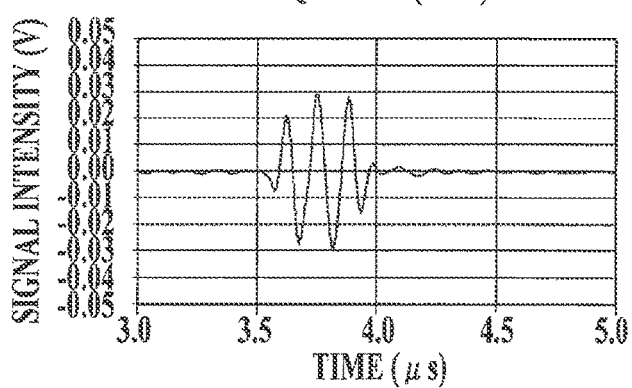
FIG. 19A is a graphical representation of a temporal change in the signal intensity of ultrasound in Comparative Example 4.
Figure 19B:
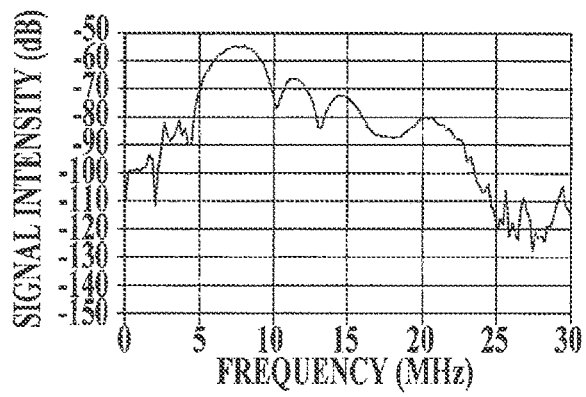
FIG. 19B illustrates the power spectrum of the ultrasound in Comparative Example 4.

The excitation signal waveform in Comparative Example 4 is referred to as waveform 4 (waveform no.: 4). FIG. 18A is a graphical representation of a temporal change in the signal intensity of an excitation signal in Comparative Example 4. FIG. 18B illustrates the power spectrum of the excitation signal in Comparative Example 4. FIG. 19A is a graphical representation of a temporal change in the signal intensity of ultrasound in Comparative Example 4. FIG. 19B illustrates the power spectrum of the ultrasound in Comparative Example 4.

The waveform of the excitation signal in Comparative Example 4 generated by the transmitter 12 has a temporal change in the signal intensity as shown in FIG. 18A. The power spectrum obtained by Fourier transform of the excitation signal shown in FIG. 18A has frequency characteristics of the signal intensity as shown in FIG. 18B. The waveform of ultrasound transmitted in response to the excitation signal in FIG. 18A which is fed to the ultrasound probe 2 has a temporal change in the signal intensity as shown in FIG. 19A. The power spectrum obtained by Fourier transform of the ultrasound shown in FIG. 19A has frequency characteristics of the signal intensity as shown in FIG. 19B.

Comparative Example 5

Figure 20A:
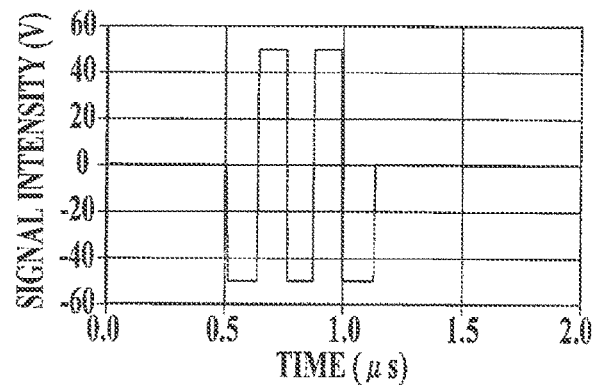
FIG. 20A is a graphical representation of a temporal change in the signal intensity of an excitation signal in Comparative Example 5.
Figure 20B:
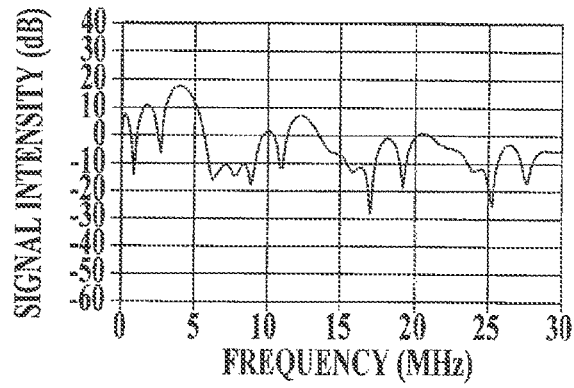
FIG. 20B illustrates the power spectrum of the excitation signal in Comparative Example 5.
Figure 21A:
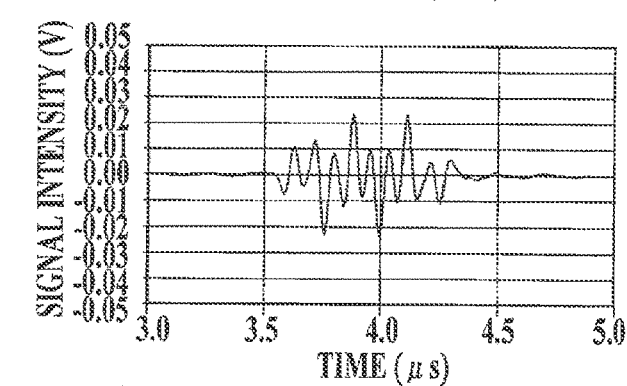
FIG. 21A is a graphical representation of a temporal change in the signal intensity of ultrasound in Comparative Example 5.
Figure 21B:
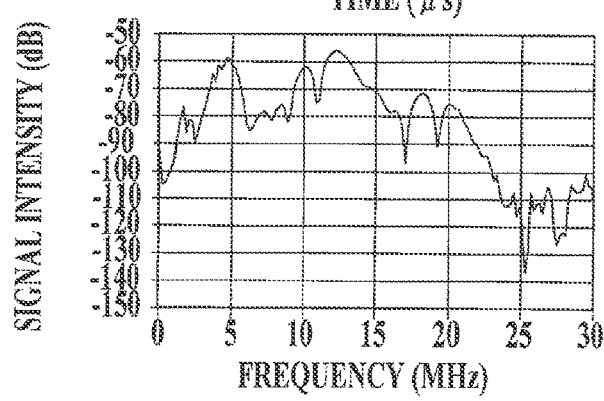
FIG. 21B illustrates the power spectrum of the ultrasound in Comparative Example 5.

The excitation signal waveform in Comparative Example 5 is referred to as waveform 5 (waveform no.: 5). FIG. 20A is a graphical representation of a temporal change in the signal intensity of an excitation signal in Comparative Example 5. FIG. 20B illustrates the power spectrum of the excitation signal in Comparative Example 5. FIG. 21A is a graphical representation of a temporal change in the signal intensity of ultrasound in Comparative Example 5. FIG. 21B illustrates the power spectrum of the ultrasound in Comparative Example 5.

The waveform of the excitation signal in Comparative Example 5 generated by the transmitter 12 has a temporal change in the signal intensity as shown in FIG. 20A. The power spectrum obtained by Fourier transform of the excitation signal shown in FIG. 20A has frequency characteristics of the signal intensity as shown in FIG. 20B. The waveform of ultrasound transmitted in response to the excitation signal in FIG. 20A which is fed to the ultrasound probe 2 has a temporal change in the signal intensity as shown in FIG. 21A. The power spectrum obtained by Fourier transform of the ultrasound shown in FIG. 21A has frequency characteristics of the signal intensity as shown in FIG. 21B.

Comparative Example 6

Figure 22A:
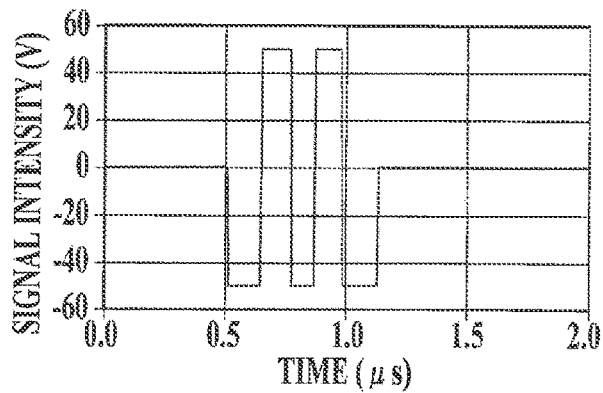
FIG. 22A is a graphical representation of a temporal change in the signal intensity of an excitation signal in Comparative Example 6.
Figure 22B:
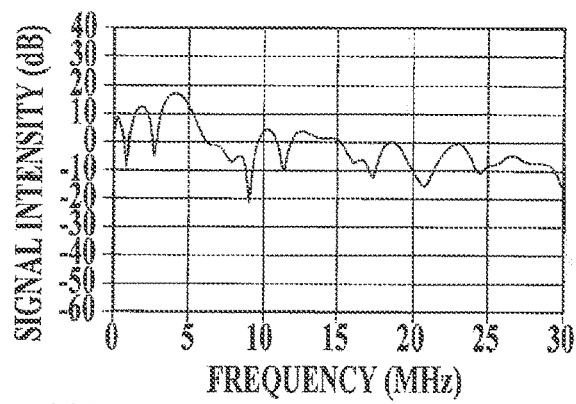
FIG. 22B illustrates the power spectrum of the excitation signal in Comparative Example 6.
Figure 23A:
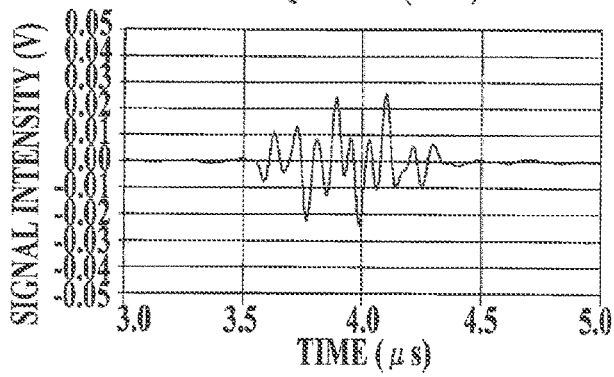
FIG. 23A is a graphical representation of a temporal change in the signal intensity of ultrasound in Comparative Example 6.
Figure 23B:
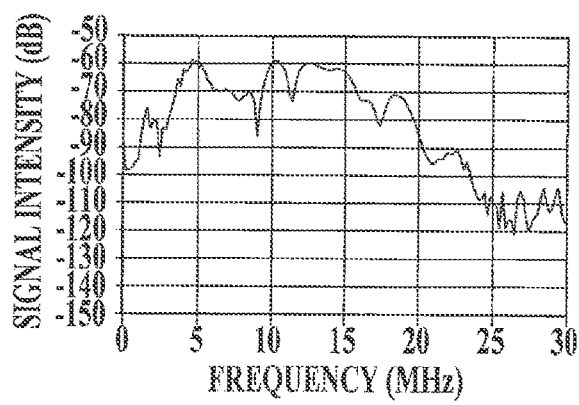
FIG. 23B illustrates the power spectrum of the ultrasound in Comparative Example 6.

The excitation signal waveform in Comparative Example 6 is referred to as waveform 6 (waveform no.: 6). FIG. 22A is a graphical representation of a temporal change in the signal intensity of an excitation signal in Comparative Example 6. FIG. 22B illustrates the power spectrum of the excitation signal in Comparative Example 6. FIG. 23A is a graphical representation of a temporal change in the signal intensity of ultrasound in Comparative Example 6. FIG. 23B illustrates the power spectrum of the ultrasound in Comparative Example 6.

The waveform of the excitation signal in Comparative Example 6 generated by the transmitter 12 has a temporal change in the signal intensity as shown in FIG. 22A. The power spectrum obtained by Fourier transform of the excitation signal shown in FIG. 22A has frequency characteristics of the signal intensity as shown in FIG. 22B. The waveform of ultrasound transmitted in response to the excitation signal in FIG. 22A which is fed to the ultrasound probe 2 has a temporal change in the signal intensity as shown in FIG. 23A. The power spectrum obtained by Fourier transform of the ultrasound shown in FIG. 23A has frequency characteristics of the signal intensity as shown in FIG. 23B.

Example 1

Figure 24A:
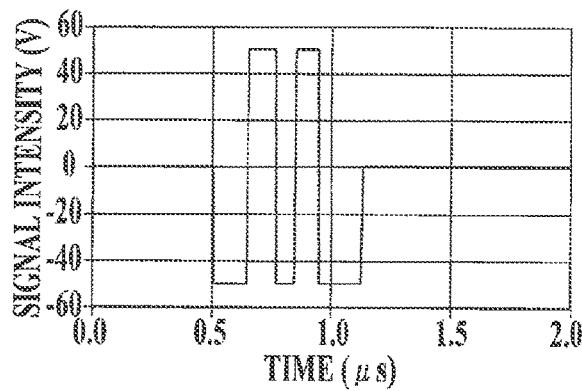
FIG. 24A is a graphical representation of a temporal change in the signal intensity of an excitation signal in Example 1.
Figure 24B:
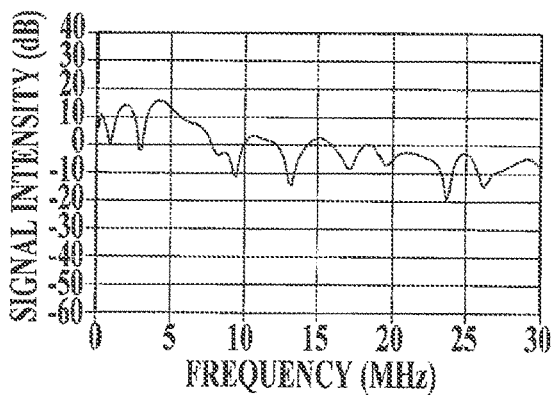
FIG. 24B illustrates the power spectrum of the excitation signal in Example 1.
Figure 25A:
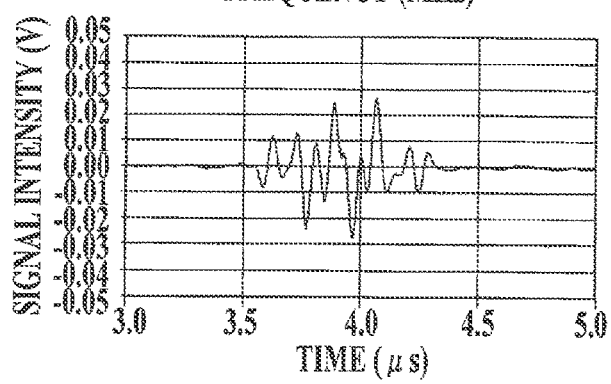
FIG. 25A is a graphical representation of a temporal change in the signal intensity of ultrasound in Example 1.
Figure 25B:
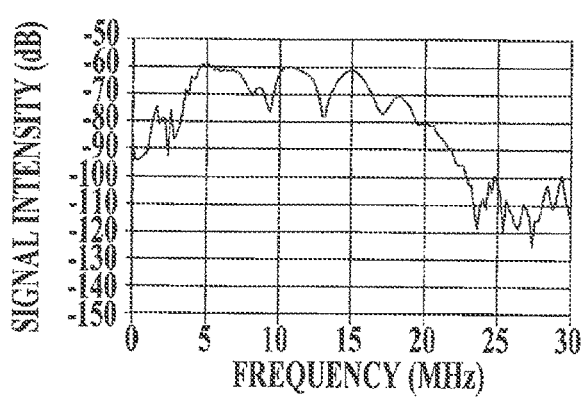
FIG. 25B illustrates the power spectrum of the ultrasound in Example 1.

The excitation signal waveform in Example 1 is referred to as waveform 7 (waveform no.: 7). FIG. 24A is a graphical representation of a temporal change in the signal intensity of an excitation signal in Example 1. FIG. 24B illustrates the power spectrum of the excitation signal in Example 1. FIG. 25A is a graphical representation of a temporal change in the signal intensity of ultrasound in Example 1. FIG. 25B illustrates the power spectrum of the ultrasound in Example 1.

The waveform of the excitation signal in Example 1 generated by the transmitter 12 has a temporal change in the signal intensity as shown in FIG. 24A. The power spectrum obtained by Fourier transform of the excitation signal shown in FIG. 24A has frequency characteristics of the signal intensity as shown in FIG. 24B. The waveform of ultrasound transmitted in response to the excitation signal in FIG. 24A which is fed to the ultrasound probe 2 has a temporal change in the signal intensity as shown in FIG. 25A. The power spectrum obtained by Fourier transform of the ultrasound shown in FIG. 25A has frequency characteristics of the signal intensity as shown in FIG. 25B.

Example 2

Figure 27A:
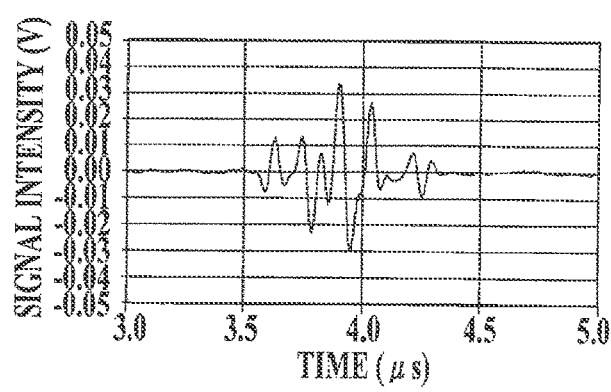
FIG. 27A is a graphical representation of a temporal change in the signal intensity of ultrasound in Example 2.
Figure 27B:
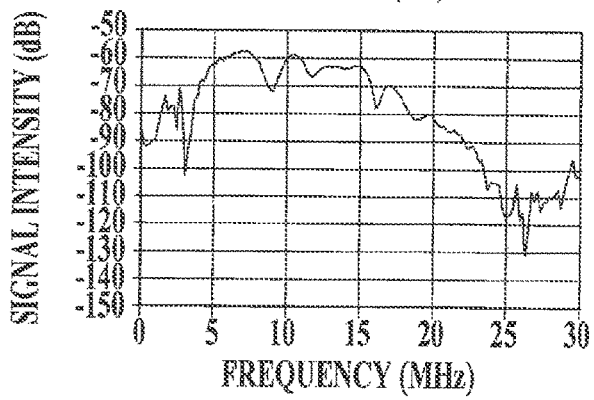
FIG. 27B illustrates the power spectrum of the ultrasound in Example 2.

The excitation signal waveform in Example 2 is referred to as waveform 8 (waveform no.: 8). FIG. 26A is a graphical representation of a temporal change in the signal intensity of an excitation signal in Example 2. FIG. 26B illustrates the power spectrum of the excitation signal in Example 2. FIG. 27A is a graphical representation of a temporal change in the signal intensity of ultrasound in Example 2. FIG. 27B illustrates the power spectrum of the ultrasound in Example 2.

The waveform of the excitation signal in Example 2 generated by the transmitter 12 has a temporal change in the signal intensity as shown in FIG. 26A. The power spectrum obtained by Fourier transform of the excitation signal shown in FIG. 26A has frequency characteristics of the signal intensity as shown in FIG. 26B. The waveform of ultrasound transmitted in response to the excitation signal in FIG. 26A which is fed to the ultrasound probe 2 has a temporal change in the signal intensity as shown in FIG. 27A. The power spectrum obtained by Fourier transform of the ultrasound shown in FIG. 27A has frequency characteristics of the signal intensity as shown in FIG. 27B.

Comparative Example 7

Figure 28A:
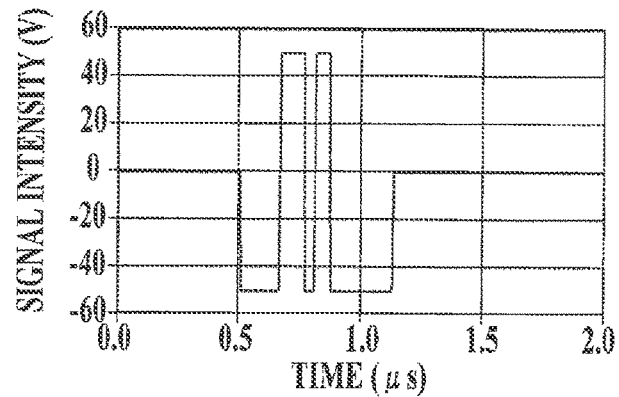
FIG. 28A is a graphical representation of a temporal change in the signal intensity of an excitation signal in Comparative Example 7.
Figure 28B:
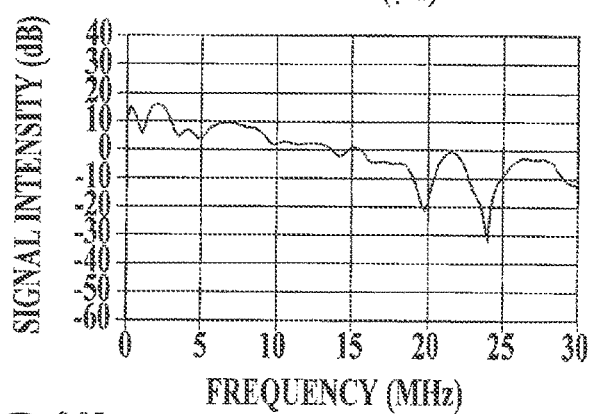
FIG. 28B illustrates the power spectrum of the excitation signal in Comparative Example 7.
Figure 29A:
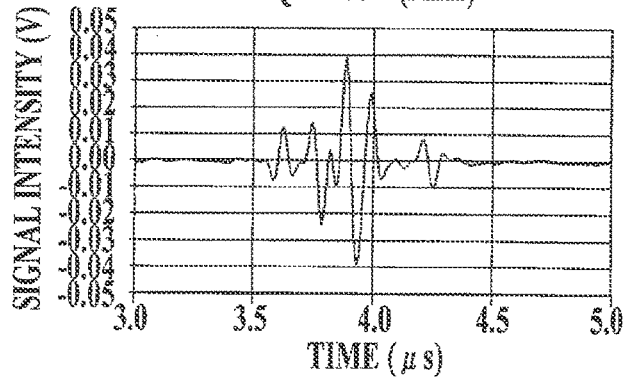
FIG. 29A is a graphical representation of a temporal change in the signal intensity of ultrasound in Comparative Example 7.
Figure 29B:
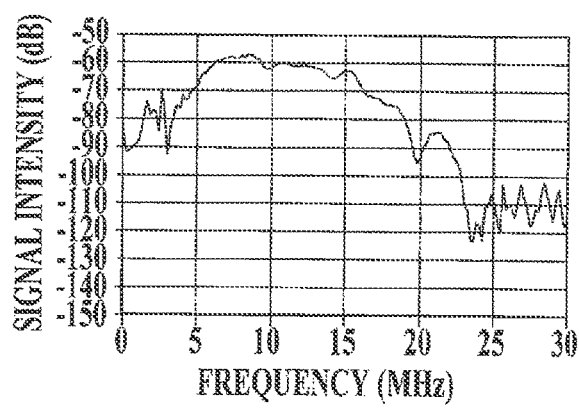
FIG. 29B illustrates the power spectrum of the ultrasound in Comparative Example 7.

The excitation signal waveform in Comparative Example 7 is referred to as waveform 9 (waveform no.: 9). FIG. 28A is a graphical representation of a temporal change in the signal intensity of an excitation signal in Comparative Example 7. FIG. 28B illustrates the power spectrum of the excitation signal in Comparative Example 7. FIG. 29A is a graphical representation of a temporal change in the signal intensity of ultrasound in Comparative Example 7. FIG. 29B illustrates the power spectrum of the ultrasound in Comparative Example 7.

The waveform of the excitation signal in Comparative Example 7 generated by the transmitter 12 has a temporal change in the signal intensity as shown in FIG. 28A. The power spectrum obtained by Fourier transform of the excitation signal shown in FIG. 28A has frequency characteristics of the signal intensity as shown in FIG. 28B. The waveform of ultrasound transmitted in response to the excitation signal in FIG. 28A which is fed to the ultrasound probe 2 has a temporal change in the signal intensity as shown in FIG. 29A. The power spectrum obtained by Fourier transform of the ultrasound shown in FIG. 29A has frequency characteristics of the signal intensity as shown in FIG. 29B.

Comparative Example 8

Figure 31A:
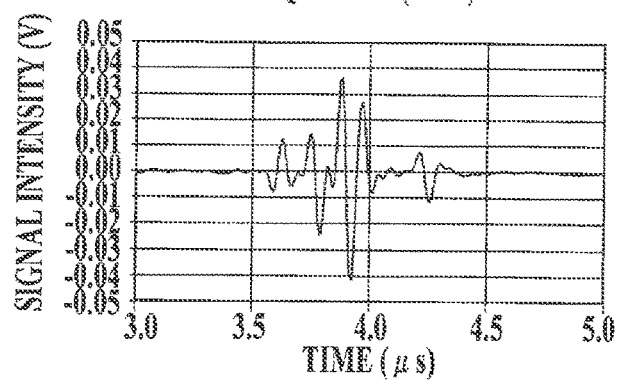
FIG. 31A is a graphical representation of a temporal change in the signal intensity of ultrasound in Comparative Example 8.
Figure 31B:
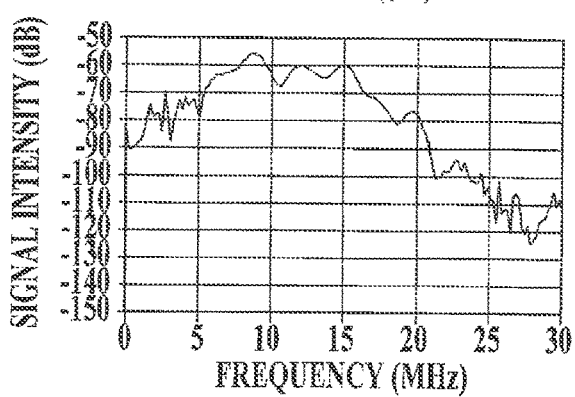
FIG. 31B illustrates the power spectrum of the ultrasound in Comparative Example 8.

The excitation signal waveform in Comparative Example 8 is referred to as waveform 10 (waveform no. 10). FIG. 30A is a graphical representation of a temporal change in the signal intensity of an excitation signal in Comparative Example 8. FIG. 30B illustrates the power spectrum of the excitation signal in Comparative Example 8. FIG. 31A is a graphical representation of a temporal change in the signal intensity of ultrasound in Comparative Example 8. FIG. 31B illustrates the power spectrum of the ultrasound in Comparative Example 8.

The waveform of the excitation signal in Comparative Example 8 generated by the transmitter 12 has a temporal change in the signal intensity as shown in FIG. 30A. The power spectrum obtained by Fourier transform of the excitation signal shown in FIG. 30A has frequency characteristics of the signal intensity as shown in FIG. 30B. The waveform of ultrasound transmitted in response to the excitation signal in FIG. 30A which is fed to the ultrasound probe 2 has a temporal change in the signal intensity as shown in FIG. 31A. The power spectrum obtained by Fourier transform of the ultrasound shown in FIG. 31A has frequency characteristics of the signal intensity as shown in FIG. 31B.

Example 3

Figure 32A:
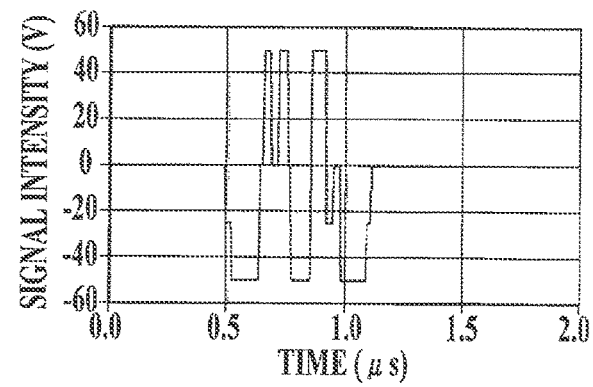
FIG. 32A is a graphical representation of a temporal change in the signal intensity of an excitation signal in Example 3.
Figure 32B:
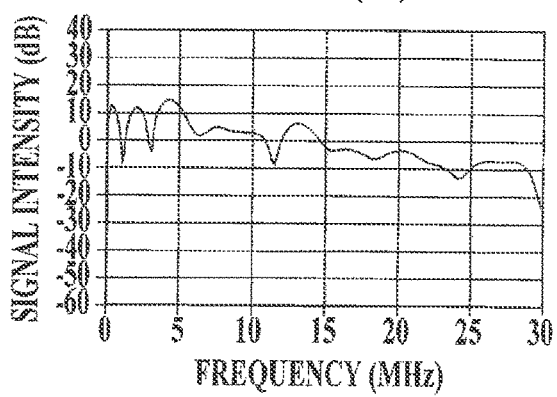
FIG. 32B illustrates the power spectrum of the excitation signal in Example 3.
Figure 33A:
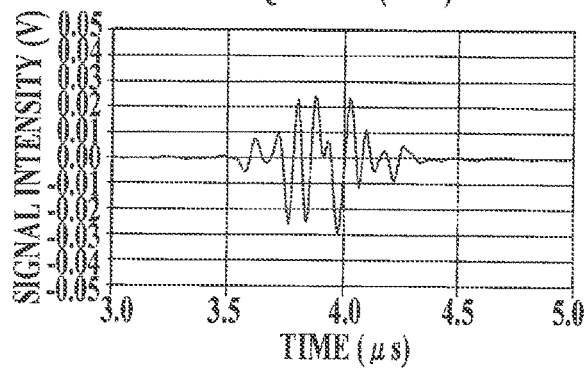
FIG. 33A is a graphical representation of a temporal change in the signal intensity of ultrasound in Example 3.
Figure 33B:
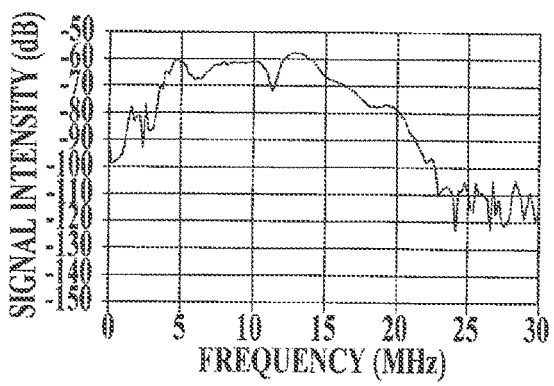
FIG. 33B illustrates the power spectrum of the ultrasound in Example 3.

The excitation signal waveform in Example 3 is referred to as waveform 11 (waveform no.: 11). FIG. 32A is a graphical representation of a temporal change in the signal intensity of an excitation signal in Example 3. FIG. 32B illustrates the power spectrum of the excitation signal in Example 3. FIG. 33A is a graphical representation of a temporal change in the signal intensity of ultrasound in Example 3. FIG. 33B illustrates the power spectrum of the ultrasound in Example 3.

The waveform of the excitation signal in Example 3 generated by the transmitter 12 has a temporal change in the signal intensity as shown in FIG. 32A. The power spectrum obtained by Fourier transform of the excitation signal shown in FIG. 32A has frequency characteristics of the signal intensity as shown in FIG. 32B. The waveform of ultrasound transmitted in response to the excitation signal in FIG. 32A which is fed to the ultrasound probe 2 has a temporal change in the signal intensity as shown in FIG. 33A. The power spectrum obtained by Fourier transform of the ultrasound shown in FIG. 33A has frequency characteristics of the signal intensity as shown in FIG. 33B.

Example 4

Figure 35A:
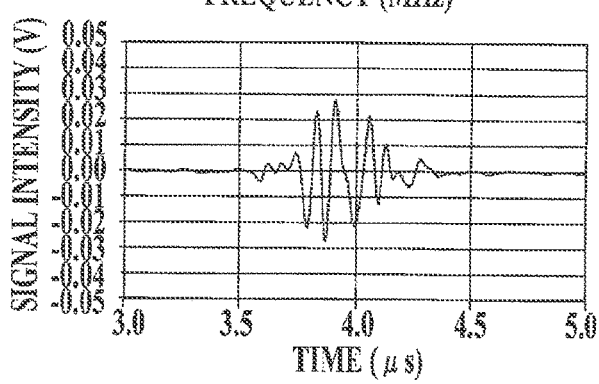
FIG. 35A is a graphical representation of a temporal change in the signal intensity of ultrasound in Example 4.
Figure 35B:
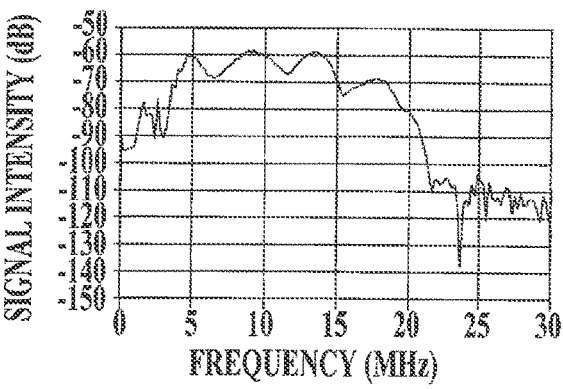
FIG. 35B illustrates the power spectrum of the ultrasound in Example 4.

The excitation signal waveform in Example 4 is referred to as waveform 12 (waveform no.: 12). FIG. 34A is a graphical representation of a temporal change in the signal intensity of an excitation signal in Example 4. FIG. 34B illustrates the power spectrum of the excitation signal in Example 4. FIG. 35A is a graphical representation of a temporal change in the signal intensity of ultrasound in Example 4. FIG. 35B illustrates the power spectrum of the ultrasound in Example 4.

The waveform of the excitation signal in Example 4 generated by the transmitter 12 has a temporal change in the signal intensity as shown in FIG. 34A. The power spectrum obtained by Fourier transform of the excitation signal shown in FIG. 34A has frequency characteristics of the signal intensity as shown in FIG. 34B. The waveform of ultrasound transmitted in response to the excitation signal in FIG. 34A which is fed to the ultrasound probe 2 has a temporal change in the signal intensity as shown in FIG. 35A. The power spectrum obtained by Fourier transform of the ultrasound shown in FIG. 35A has frequency characteristics of the signal intensity as shown in FIG. 35B.

Example 5

Figure 36A:
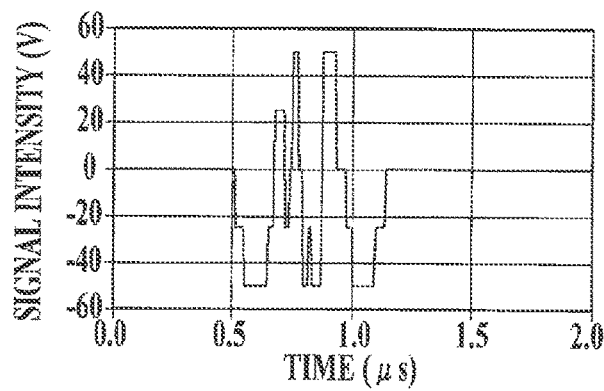
FIG. 36A is a graphical representation of a temporal change in the signal intensity of an excitation signal in Example 5.
Figure 36B:
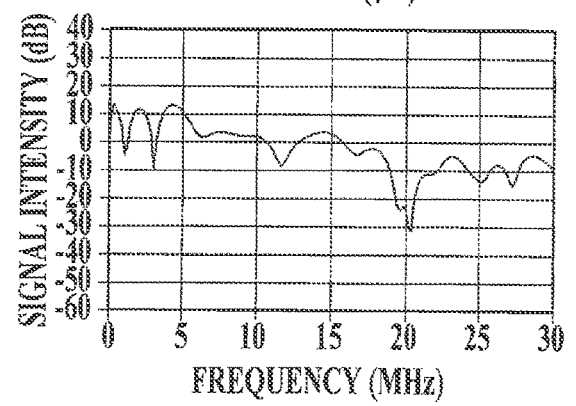
FIG. 36B illustrates the power spectrum of an excitation signal in Example 5.
Figure 37A:
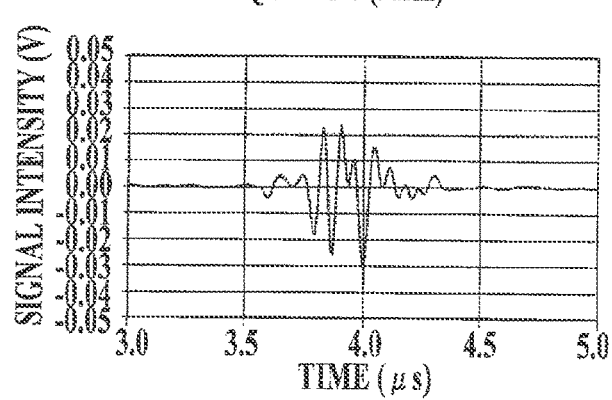
FIG. 37A is a graphical representation of a temporal change in the signal intensity of ultrasound in Example 5.
Figure 37B:
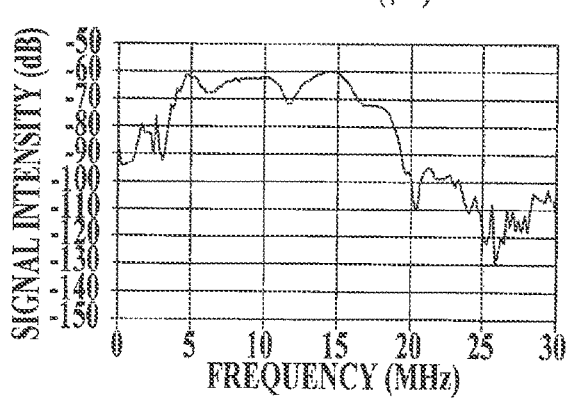
FIG. 37B illustrates the power spectrum of the ultrasound in Example 5.

The excitation signal waveform of Example 5 is referred to as waveform 13 (waveform no.: 13). FIG. 36A is a graphical representation of a temporal change in the signal intensity of an excitation signal in Example 5. FIG. 36B illustrates the power spectrum of the excitation signal in Example 5. FIG. 37A is a graphical representation of a temporal change in the signal intensity of ultrasound in Example 5. FIG. 37B illustrates the power spectrum of the ultrasound in Example 5.

The waveform of the excitation signal in Example 5 generated by the transmitter 12 has a temporal change in the signal intensity as shown in FIG. 36A. The power spectrum obtained by Fourier transform of the excitation signal shown in FIG. 36A has frequency characteristics of the signal intensity as shown in FIG. 36B. The waveform of ultrasound transmitted in response to the excitation signal in FIG. 36A which is fed to the ultrasound probe 2 has a temporal change in the signal intensity as shown in FIG. 37A. The power spectrum obtained by Fourier transform of the ultrasound shown in FIG. 37A has frequency characteristics of the signal intensity as shown in FIG. 37B.

Comparative Example 9

Figure 38A:
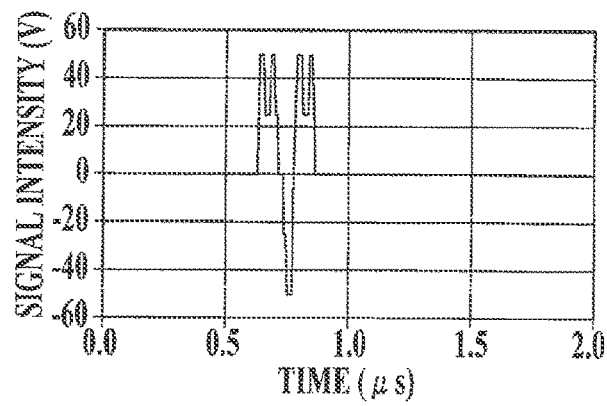
FIG. 38A is a graphical representation of a temporal change in the signal intensity of an excitation signal in Comparative Example 9.
Figure 38B:
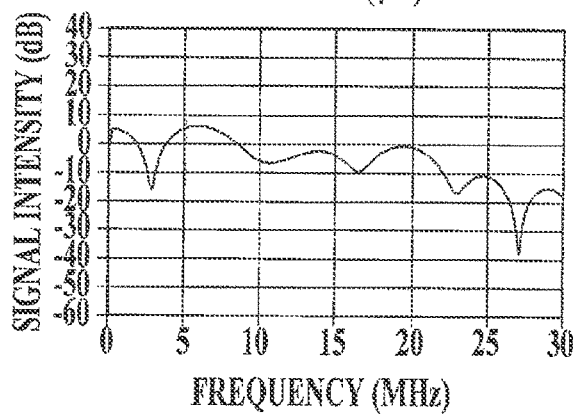
FIG. 38B illustrates the power spectrum of the excitation signal in Comparative Example 9.
Figure 39A:
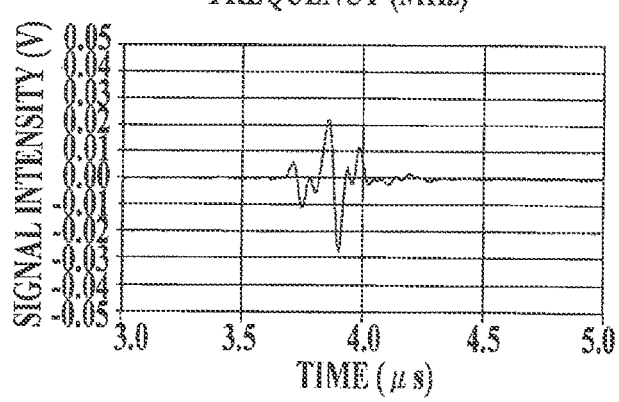
FIG. 39A is a graphical representation of a temporal change in the signal intensity of ultrasound in Comparative Example 9.
Figure 39B:
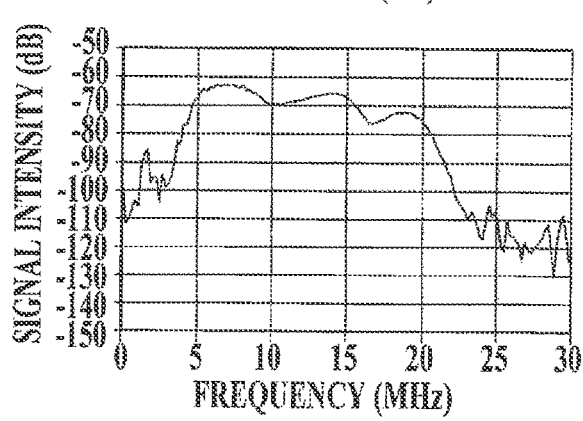
FIG. 39B illustrates the power spectrum of the ultrasound in Comparative Example 9.

The excitation signal waveform in Comparative Example 9 is referred to as waveform 14 (waveform no.: 14). FIG. 38A is a graphical representation of a temporal change in the signal intensity of an excitation signal in Comparative Example 9. FIG. 38B illustrates the power spectrum of the excitation signal in Comparative Example 9. FIG. 39A is a graphical representation of a temporal change in the signal intensity of ultrasound in Comparative Example 9. FIG. 39B illustrates the power spectrum of the ultrasound in Comparative Example 9.

The waveform of the excitation signal in Comparative Example 9 generated by the transmitter 12 has a temporal change in the signal intensity as shown in FIG. 38A. The power spectrum obtained by Fourier transform of the excitation signal shown in FIG. 38A has frequency characteristics of the signal intensity as shown in FIG. 38B. The waveform of ultrasound transmitted in response to the excitation signal in FIG. 38A which is fed to the ultrasound probe 2 has a temporal change in the signal intensity as shown in FIG. 39A. The power spectrum obtained by Fourier transform of the ultrasound shown in FIG. 39A has frequency characteristics of the signal intensity as shown in FIG. 39B.

Comparative Example 10

Figure 40A:
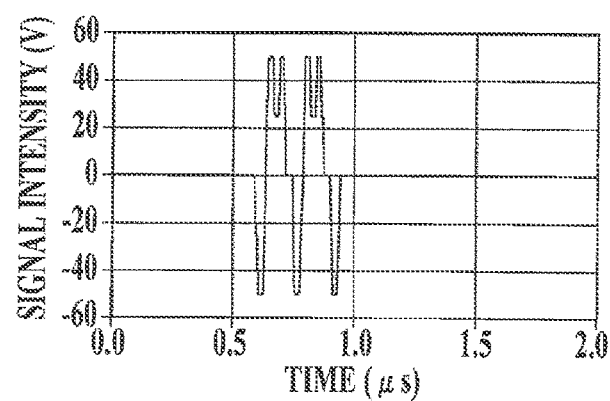
FIG. 40A is a graphical representation of a temporal change in the signal intensity of an excitation signal in Comparative Example 10.
Figure 40B:
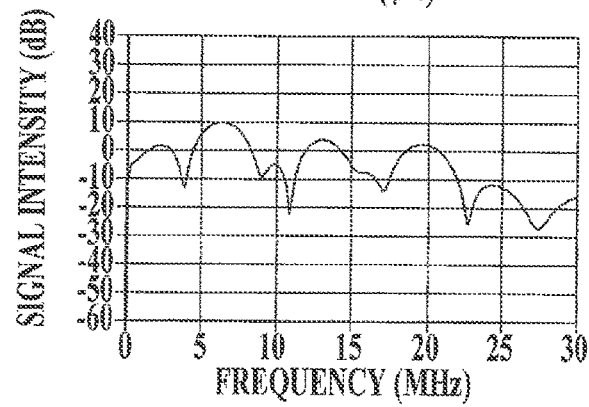
FIG. 40B illustrates the power spectrum of the excitation signal in Comparative Example 10.
Figure 41A:
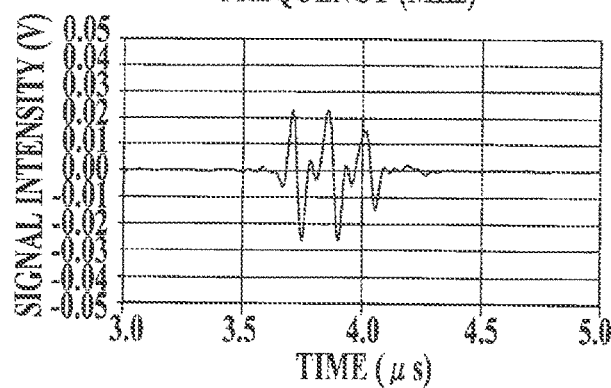
FIG. 41A is a graphical representation of a temporal change in the signal intensity of ultrasound in Comparative Example 10.
Figure 41B:
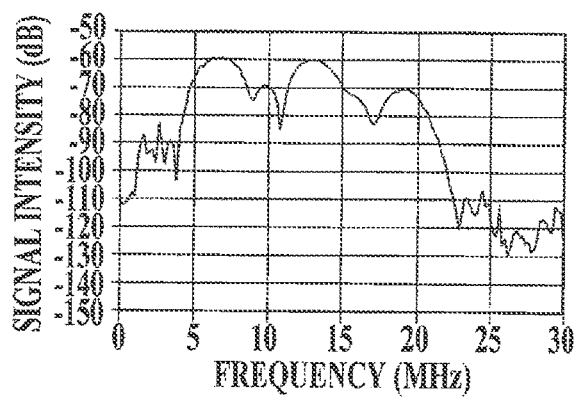
FIG. 41B illustrates the power spectrum of the ultrasound in Comparative Example 10.

The excitation signal waveform in Comparative Example 10 is referred to as waveform 15 (waveform no.: 15). FIG. 40A is a graphical representation of a temporal change in the signal intensity of an excitation signal in Comparative Example 10. FIG. 40B illustrates the power spectrum of the excitation signal in Comparative Example 10. FIG. 41A is a graphical representation of a temporal change in the signal intensity of ultrasound in Comparative Example 10. FIG. 41B illustrates the power spectrum of the ultrasound in Comparative Example 10.

The waveform of the excitation signal in Comparative Example 10 generated by the transmitter 12 has a temporal change in the signal intensity as shown in FIG. 40A. The power spectrum obtained by Fourier transform of the excitation signal shown in FIG. 40A has frequency characteristics of the signal intensity as shown in FIG. 40B. The waveform of ultrasound transmitted in response to the excitation signal in FIG. 40A which is fed to the ultrasound probe 2 has a temporal change in the signal intensity as shown in FIG. 41A. The power spectrum obtained by Fourier transform of the ultrasound shown in FIG. 41A has frequency characteristics of the signal intensity as shown in FIG. 41B.

Evaluation of Image Quality

Tables 1 to 3 indicate the values of indexes for the excitation signals and ultrasounds in Examples 1 to 5 and Comparative Examples 1 to 10 and the results of the evaluated quality of the ultrasound images created from the image data generated with the excitation signals and ultrasounds in the ultrasound image diagnostic apparatus S.

TABLE 1

| | | Excitation Signal Waveform | | | | | | | | |
|---|---|---|---|---|---|---|---|---|---|---|
| | | Temporal Waveform Characteristics | | | | | | Frequency Characteristics in −6 dB Transmission Bandwidth of Ultrasound Probe | | |
| | Waveform No. | Excitation Time (nsec) | Nbr. of Waves at TxFL6 | Each Part Time (nsec) | Frequency Converted at 0.5 Waveform (MHz) | FC6 Frequency Rate | Standard Deviation of Converted Frequency | Frequency At: Maximum Intensity (MHz) | Standard Deviation of Normalized Signal Intensity | Signal Intensity at Frequency TxFL6 (dB) |
| Comparison 1 | 1 | 375 | 1.88 | 125, 125, 125 | 4.0, 4.0, 4.0 | 0.39, 0.39, 0.39 | 0.000 | 3.7 | 10.7 | 9.9 |
| Comparison 2 | 2 | 625 | 3.13 | 125, 125, 125, 125, 125 | 4.0, 4.0, 4.0, 4.0, 4.0 | 0.39, 0.39, 0.39, 0.39, 0.39 | 0.000 | 4.0 | 8.0 | 9.3 |
| Comparison 3 | 3 | 500 | 2.50 | 100, 100, 100, 100, 100 | 5.0, 5.0, 5.0, 5.0, 5.0 | 0.49, 0.49, 0.49, 0.49, 0.49 | 0.000 | 5.0 | 9.6 | 16.0 |
| Comparison 4 | 4 | 357 | 1.79 | 71, 71, 71, 71, 71 | 7.0, 7.0, 7.0, 7.0, 7.0 | 0.68, 0.68, 0.68, 0.68, 0.68 | 0.000 | 7.0 | 10.7 | 2.9 |
| Comparison 5 | 5 | 625 | 3.13 | 137, 119, 113, 125, 131 | 3.6, 4.2, 4.4, 4.0, 3.8 | 0.35, 0.41, 0.43, 0.39, 0.37 | 0.027 | 4.0 | 8.2 | 11.2 |
| Comparison 6 | 6 | 625 | 3.13 | 150, 113, 102, 124, 136 | 3.3, 4.4, 4.9, 4.0, 3.7 | 0.33, 0.43, 0.48, 0.39, 0.36 | 0.053 | 4.0 | 5.8 | 12.4 |

TABLE 1-continued

| | | Ultrasound Waveform | | | | |
|---|---|---|---|---|---|---|
| | | Temporal Waveform Characteristics | | Frequency Characteristics in −6 dB Transmission Bandwidth of Ultrasound Probe | | |
| | | Wave Packet Duration (nsec) | Nbr. of Waves at TxFL6 | Frequency At Maximum Intensity (MHz) | Standard Deviation of Normalized signal Intensity | Normalized Signal Intensity at Frequency TxFL6 (dB) |
| | Comparison 1 | 466 | 2.33 | 4.8 | 10.8 | −3.2 |
| | Comparison 2 | 720 | 3.60 | 4.8 | 8.5 | −8.61 |
| | Comparison 3 | 553 | 2.77 | 5.4 | 8.2 | −1.63 |
| | Comparison 4 | 396 | 1.98 | 8.0 | 9.9 | −15.91 |
| | Comparison 5 | 734 | 3.67 | 4.4 | 9.1 | −5.66 |
| | Comparison 6 | 744 | 3.72 | 4.8 | 6.2 | −2.1 |

TABLE 2

| | | Excitation Signal Waveform | | | | | | | |
|---|---|---|---|---|---|---|---|---|---|
| | | Temporal Waveform Characteristics | | | | | Frequency Characteristics in −6 dB Transmission Bandwidth of Ultrasound Probe | | |
| | Waveform No. | Excitation Time (nsec) | Nbr. of Waves at TxFL6 | Each Part Time (nsec) | Frequency Converted at 0.5 Waveform (MHz) | FC6 Frequency Rate | Standard Deviation of Converted Frequency | Frequency At: Maximum Intensity (MHz) | Standard Deviation of Normalized Signal Intensity | Signal Intensity at Frequency TxFL6 (dB) |
| Example 1 | 7 | 625 | 3.13 | 174, 101, 84, 121, 145 | 2.9, 5.0, 6.0, 4.1, 3.4 | 0.28, 0.48, 0.58, 0.40, 0.34 | 0.107 | 4.0 | 6.0 | 13.0 |
| Example 2 | 8 | 625 | 3.13 | 219, 80, 57, 112, 157 | 2.3, 6.3, 8.8, 4.5, 3.2 | 0.22, 0.61, 0.85, 0.44, 0.31 | 0.225 | 4.2 | 5.7 | 10.4 |
| Comparison 7 | 10 | 625 | 3.13 | 259, 63, 40, 101, 162 | 1.9, 7.9, 12.6, 4.9, 3.1 | 0.19, 0.77, 1.23, 0.48, 0.30 | 0.375 | 6.6 | 4.3 | 4.0 |
| Comparison 8 | 11 | 625 | 3.13 | 277, 56, 33, 96, 163 | 1.8, 8.9, 15.1, 5.2, 3.1 | 0.18, 0.87, 1.47, 0.51, 0.30 | 0.466 | 8.8 | 3.9 | −7.3 |
| Example 3 | 12 | 625 | 3.13 | — | — | — | — | 4.2 | 4.0 | 11.3 |
| Example 4 | 13 | 610 | 3.05 | — | — | — | — | 4.2 | 4.7 | 11.5 |
| Example 5 | 14 | 640 | 3.20 | — | — | — | — | 4.2 | 3.7 | 10.6 |
| Comparison 9 | 15 | 245 | 1.23 | — | — | — | — | 5.8 | 4.7 | 5.6 |
| Comparison 10 | 16 | 364 | 1.82 | — | — | — | — | 6.4 | 7.7 | 6.3 |

TABLE 2-continued

| | | Ultrasound Waveform | | | | |
|---|---|---|---|---|---|---|
| | | Temporal Waveform Characteristics | | Frequency Characteristics in −6 dB Transmission Bandwidth of Ultrasound Probe | | |
| | | Wave Packet Duration (nsec) | Nbr. of Waves at TxFL6 | Frequency At Maximum Intensity (MHz) | Standard Deviation of Normalized signal Intensity | Normalized Signal Intensity at Frequency TxFL6 (dB) |
| | Example 1 | 733 | 3.67 | 4.8 | 5.3 | −0.84 |
| | Example 2 | 682 | 3.41 | 7.8 | 4.8 | −5.24 |
| | Comparison 7 | 647 | 3.24 | 8.6 | 4.2 | −11.39 |
| | Comparison 8 | 649 | 3.25 | 9.0 | 4.6 | −23.48 |
| | Example 3 | 622 | 3.11 | 13.0 | 4.1 | −4.16 |
| | Example 4 | 504 | 2.52 | 13.4 | 4.6 | −2.8 |
| | Example 5 | 541 | 2.71 | 14.4 | 3.6 | −2.58 |
| | Comparison 9 | 295 | 1.48 | 6.8 | 3.7 | −4.66 |
| | Comparison 10 | 413 | 2.07 | 6.4 | 7.0 | −7.69 |

TABLE 3

Evaluation Results of Image Quality

| | Phantom-PSF | | Speckle Uniformity (Brightness Standard Deviation) | | Phantom- Penetration Depth (mm) | Visualization Score | | | |
|---|---|---|---|---|---|---|---|---|---|
| | Distance Resolution (μm) | Azimuthal Resolution (μm) | 10 mm Depth | 35 mm Depth | | Wrist | MP Joint Flexor Tendon | Infrapatellar Fat Body | Lower Extremities (Musculus Gastrocnemius and Soleus) |
| Comparison 1 | 334 | 605 | 16.1 | 17.3 | 53 | 5.4 | 5.2 | 5.6 | 5.0 |
| Comparison 2 | 430 | 585 | 16.5 | 18.2 | 66 | 5.2 | 4.6 | 5.2 | 6.6 |
| Comparison 3 | 402 | 560 | 15.5 | 17.5 | 63 | 5.6 | 5.1 | 5.0 | 6.0 |
| Comparison 4 | 290 | 507 | 13.3 | 18.0 | 45 | 7.6 | 8.0 | 3.2 | 3.0 |
| Comparison 5 | 390 | 580 | 16.2 | 16.8 | 63 | 5.4 | 5.0 | 5.4 | 6.4 |
| Comparison 6 | 365 | 575 | 15.6 | 16.7 | 64 | 5.8 | 6.9 | 6.6 | 6.6 |
| Example 1 | 205 | 560 | 13.1 | 13.9 | 72 | 7.0 | 8.6 | 8.0 | 8.0 |
| Example 2 | 195 | 502 | 12.9 | 13.8 | 76 | 9.0 | 9.0 | 8.4 | 8.4 |
| Comparison 7 | 270 | 522 | 13.4 | 15.2 | 51 | 7.0 | 8.0 | 6.0 | 6.0 |
| Comparison 8 | 290 | 501 | 13.6 | 16.7 | 45 | 6.8 | 7.6 | 5.8 | 5.5 |
| Example 3 | 210 | 488 | 13.1 | 13.6 | 77 | 9.0 | 8.4 | 8.6 | 8.8 |
| Example 4 | 230 | 545 | 13.4 | 14.0 | 72 | 8.2 | 8.0 | 8.1 | 7.0 |
| Example 5 | 241 | 510 | 13.8 | 14.4 | 70 | 8.3 | 7.4 | 8.2 | 7.2 |
| Comparison 9 | 190 | 480 | 12.8 | 15.6 | 47 | 9.2 | 9.2 | 5.2 | 4.4 |
| Comparison 10 | 295 | 470 | 13.3 | 16.1 | 52 | 7.0 | 7.1 | 6.0 | 4.8 |

The definition of each index in Tables 1 to 3 and the method of calculation will now be described.

Each item of "Temporal Waveform Characteristics" of an excitation signal waveform will now be described.

The signal intensity of an excitation signal waveform (signal intensity of frequency components) is based on a converted frequency obtained as follow, regardless of actual driving voltage: The actual driving voltage is multiplied by a multiplying factor such that positive and negative maximum voltages are ±50 [V] to acquire an excitation signal waveform to be converted and then a 5 [μsec] time domain that includes the excitation signal waveform is converted into a frequency. If the absolute positive and negative maximum voltages are unequal, the multiplying factor is selected such that a larger absolute voltage is 50 [V] or less to acquire an excitation signal waveform to be converted.

"Excitation Time [nsec]" of "Excitation Signal Waveform" is a period from the time at which the absolute voltage first reaches 5 [V] to the time at which the absolute voltage last falls below 5 [V] in the excitation signal waveform to be converted.

"Nbr. of Waves at TxFL6" of "Excitation Signal Waveform" is the wavenumber obtained by dividing the excitation time of the excitation signal waveform by the period at the lower limit frequency (TxFL6) of the −6 dB transmission and reception bandwidth of the ultrasound probe 2. "Each Part Time" of "Excitation Signal Waveform" is the duration of each part [nsec] of the excitation signal waveform to be converted. "Frequency Converted at 0.5 Waveforms" of "Excitation Signal Waveform" is frequency [MHz] into which parts of the excitation signal waveform are converted with each part regarded as 0.5 waveforms. "FC6 Frequency Rate" of "Excitation Signal Waveform" is a value normalized by dividing the frequency into which the excitation signal waveform is converted at 0.5 waveforms by the central frequency FC6 of the −6 dB transmission and reception bandwidth of the ultrasound probe 2.

"Standard Deviation of Converted Frequency" of "Excitation Signal Waveform", which is based on the signal intensity of frequency components of the excitation signal waveform, is calculated from the signal intensity of frequency components for a given interval with the following expression (1).

[Expression 1]

$$\sqrt{\frac{\sum (x-\bar{x})^2}{n}} \quad (1)$$

x is the value of sample, $\bar{x}$ is average, and n is the number of samples.

Example 3 to 5 and Comparative Example 9 and 10 in Table 2 have no value for "Each Part Time", "Frequency Converted at 0.5 Waveforms", "FC6 Frequency Rate", and "Standard Deviation of Converted Frequency" of "Temporal Waveform Characteristics" of "Excitation Signal Waveform" since the excitation signal is not a square wave.

Each item of "Frequency Characteristics in −6 dB Transmission Bandwidth of Ultrasound Probe" of "Excitation Signal Waveform" in Tables 1 and 2 will now be described.

"Frequency at Maximum Intensity" of "Excitation Signal Waveform" is a frequency [MHz] at the maximum signal intensity (sensitivity) of an excitation signal in the −6 dB transmission bandwidth of the ultrasound probe 2. "Standard Deviation of Normalized Signal Intensity" of "Excitation Signal Waveform" is a standard deviation, calculated with expression (1), of the signal intensity (sensitivity) of the excitation signal waveform normalized such that the maximum signal intensity in the −6 dB transmission bandwidth of the ultrasound probe 2 is 0 [dB]. "Signal Intensity at Frequency TxFL6" of "Excitation Signal Waveform" is the absolute signal intensity (sensitivity) [dB] of the excitation signal at a frequency TxFL6 in the −6 dB transmission bandwidth of the ultrasound probe 2.

Each item under "Temporal Waveform Characteristics" of "Ultrasound Waveform" in Tables 1 and 2 will now be described.

Only one transducer of the ultrasound probe 2 is driven with a given excitation signal waveform to send ultrasound. The ultrasound is received in water by a hydrophone having a bandwidth of 30 [MHz] or higher at a distance of 3 [mm] or less. The temporal voltage waveform of the received ultrasound is used to convert a 5 [μsec] time domain, including the ultrasound signal, into frequency. The signal intensity of the resulting frequency components is normalized such that the maximum intensity is 0 [dB]. A signal intensity of −60 [dB] is normalized into −10 [dB] with respect to the maximum intensity of frequency components set to −50 [dB].

"Wave Packet Duration" of "Ultrasound Waveform", which is based on the maximum absolute voltage of the temporal voltage waveform of the ultrasound, is a period from the time at which the absolute voltage first reaches one-fifth of the maximum absolute voltage to the time at which the absolute voltage last falls below one-fifth of the maximum absolute voltage. In other words, if the maximum voltage is set to 1 [mV], the wave packet duration is a period [nsec] from the time at which the absolute voltage first reaches ±0.2 [mV] to the time at which it last falls below ±0.2 [mV].

"Nbr. of Waves at TxFL6" of "Ultrasound Waveform." is obtained by dividing the wave packet duration of an ultrasound waveform by the period at the lower limit frequency (TxFL6) of the −6 dB transmission and reception bandwidth of the ultrasound probe 2.

Each item of "Frequency Characteristics in −6 dB Transmission Bandwidth of Ultrasound Waveform of Ultrasound Probe" of "Ultrasound Waveform" in Tables 1 and 2 will now be described.

"Frequency at Maximum Intensity" of "Ultrasound Waveform" is a frequency [MHz] at the maximum signal intensity (sensitivity) of ultrasound in the −6 dB transmission bandwidth of the ultrasound probe 2. "Standard Deviation of Normalized Signal Intensity" of "Ultrasound Waveform", which is based on the normalized signal intensity of frequency components of the ultrasound, is a standard deviation calculated from the signal intensity of frequency components in the −6 dB transmission bandwidth of the ultrasound probe 2 with the expression (1). "Normalized Signal Intensity at Frequency TxFL6" of "Ultrasound Waveform" is based on the normalized signal intensity of frequency components of ultrasound and is the normalized signal intensity of the frequency components [dB] of the ultrasound at a frequency TxFL6 in the −6 dB transmission bandwidth of the ultrasound probe 2.

Each item of "Results of Evaluated Image Quality" in Table 3 will now be described.

"Phantom-PSF (Point Spread Function)" of "Results of Evaluated Image Quality" is resolution at 20 dB (distance resolution [μm] and azimuthal resolution [μm]), which is obtained as the results of the following image quality evaluation: An SUS (stainless) wire of 50 μm is embedded in a material having the same acoustic characteristics as those of Gammex RMI 404GS-LE0.5 at the depth of 15 mm; ultrasound is transmitted and received with a transmission focal distance of 15 mm to generate an ultrasound image from image data; and the visualization brightness of the wire in the generated image data is converted into sound intensity [dB].

"Speckle Uniformity" of "Results of Evaluated Image Quality" is obtained as follows: Ultrasound is transmitted to a matrix in Gammex RMI 404GS-LE0.5 with a transmission focal distance of 30 mm and a reflected ultrasound is received to generate an image of the matrix; and the generated image data is used to evaluate the speckle uniformity. Table 3 shows the standard deviation of brightness for each of two locations: A 10 mm×10 mm area at an image data depth of 10 mm and a 10 mm×10 mm area at a depth of 35 mm. A smaller standard deviation indicates speckles in the matrix are visualized more finely and more uniformly. No significant difference between the 10 mm-depth area and the 35 mm-depth area indicates a uniform visualization in the depth direction.

"Phantom-Penetration Depth" of "Results of Evaluated Image Quality" is a penetration depth [mm] which is obtained by the following method of evaluating the image quality: Ultrasound is transmitted to a material having the same acoustic characteristics as those of Gammex RMI 403GS-LE0.5 with a transmission focal distance of 15 mm and the reflected ultrasound is received to generate an image; two consecutive frames in the generated image data are obtained; and a depth at which a correlation between the ultrasound images in the two frames is less than 0.5 is acquired as a penetration depth.

Each site ("Wrist", "Metacarpophalangeal joint (MP) Flexor Tendon", "Infrapatellar Fat Body" and "Lower Extremities (*Musculus gastrocnemius* and *Soleus*)" of "Visualization Score", which is an evaluation score of image quality, will now be described. This method of evaluating the image quality involves ultrasound transmission and reception and imaging of each site (wrist, MP joint flexor tendon, infrapatellar fat body, and lower extremities (musculus gastrocnemius and musculus soleus)) of a subject and evaluation of the ultrasound image created from generated image data by a total of ten persons including orthopedic specialists and clinical laboratory technicians, in accordance with the following evaluation criteria to obtain visualization scores for each site. The visualization scores are averaged to obtain a visualization score for each site as the result of image quality evaluation (by rounding it off to one decimal place). The visualization score corresponds to the following visualization levels:

10: Visualization level is excellent for recognizing the tissue condition.
8: Visualization level is practically sufficient for recognizing the tissue condition.
6: Visualization level is not satisfactory but enough to recognize the tissue condition.
4: Visualization level involves a slight difficulty in recognition of the tissue condition.
2: Visualization level involves a significant difficulty in recognition of the tissue condition.

Of these sites, the wrist and MP joint flexor tendon, which are disposed in a shallow site, are available for evaluation of the resolution and signal-to-noise ratio of the shallow site. Meanwhile, the infrapatellar fat body, which is disposed in a deep site, is available for evaluation of the resolution and signal-to-noise ratio of the deep site. For the lower extremities (musculus gastrocnemius and musculus soleus), which extend from shallow to deep sites, their visualization uniformity from the shallow to deep sites affect their visualization score.

As shown in "Nbr. of Waves at TxFL6", "Standard Deviation of Normalized Signal Intensity", and "Normalized Signal Intensity at Frequency TxFL6" of "Ultrasound" in Tables 1 and 2, Examples 1 to 5 satisfy all of the following requirements: The wave packet duration of ultrasound is equivalent to or more than the length of 1.5 waveforms at the lower limit frequency (TxFL6) of the −6 dB transmission bandwidth of the ultrasound probe 2; normalized signal intensity of frequency components in the −6 dB transmission bandwidth of ultrasound has a standard deviation of 6 or less; and the normalized signal intensity of frequency components at the lower limit frequency (TxFL6) in the −6 dB transmission bandwidth is −8 [dB] or higher. In contrast, Comparative Examples 1 to 10 do not satisfy at least any one of these conditions.

As shown in "Nbr. of Waves at TxFL6", "Standard Deviation of Normalized Signal Intensity" and "Signal Intensity at Frequency TxFL6" of "Excitation Signal Waveform" in Tables 1 and 2, Examples 1 to 5 satisfy all the following requirements: A excitation time of the excitation signals is equivalent to or more than the length of 1.5 waveforms at the lower limit frequency (TxFL6) of the −6 dB transmission bandwidth of the ultrasound probe 2; the signal intensity of frequency components in the −6 dB transmission bandwidth of the excitation signal has a standard deviation of 7 or less; and the signal intensity of components at the lower limit frequency in the −6 dB transmission bandwidth is 10 [dB] or higher. In contrast, Comparative Examples 1 to 10 do not satisfy at least any one of these conditions.

As shown in "Nbr. of Waves at TxFL6" and "Standard Deviation of Converted Frequency" of "Excitation Signal Waveform" in Tables 1 and 2, Examples 1 to 2 satisfy all the following requirements: A excitation time of the excitation signal is equivalent to or more than the length of 1.5 waveforms at the lower limit frequency (TxFL6) of the −6 dB transmission bandwidth of the ultrasound probe 2; the duration of parts of the excitation signal is converted into a frequency with the duration of each part regarded as 0.5 waveforms, the converted frequency is normalized with respect to the central frequency FC6 of the −6 dB transmission and reception bandwidth, and the normalized frequency has a standard deviation ranging from 0.1 to 0.3. In contrast, Comparative Examples 1 to 10 do not satisfy at least any one of these conditions.

As shown in "Each Part" of the excitation signals in Examples 1 and 2 in Table 2, the maximum part of the excitation time is preferably the first or last part. If the maximum part is not in the first or last part, that is, an excitation signal having lowest-frequency components is not transmitted during the first or last part, an excitation signal having higher frequency components is transmitted before and after the transmission of an excitation signal having lower frequency components. This precludes the transmission of ultrasound with high-frequency components localized as shown in FIG. 6A. Both the first and last parts of the excitation time are preferably the maximum part in all the parts.

As shown in "Each Part" of the excitation signals in Examples 1 and 2 in Table 2, all the parts between the first and last parts of the excitation time are preferably shorter than the first and last parts for the same reasons.

As shown in "Results of Evaluated Image Quality" of the excitation signals in Table 3, Examples 1 to 5 have a higher (shorter) distance resolution than Comparative Examples 1 to 8, a higher (shorter) azimuthal resolution than Comparative Examples 1 to 3, 5 and 6, and a greater penetration depth than Comparative Examples 1 to 10. For speckle uniformity, Examples 1 to 5 have smaller standard deviations than Comparative Examples 1 to 8 and 10, which results indicate high definition and uniform visualization. Examples 1 to 5 has no significant difference in speckle uniformity between the 10 mm-depth area and the 35 mm-depth area, as compared with Comparative Examples 1 to 10, which results indicate uniform visualization in the depth direction.

For the wrist and the MP joint flexor tendon, Examples 1 to 5 have a higher visualization score than Comparative Examples 1 to 3 and 5 to 10, which results indicate a high resolution and a signal-to-noise ratio in the visualization of shallow sites. For infrapatellar fat body, Examples 1 to 5 have a high visualization score than Comparative Examples 1 to 10, which results indicate a high resolution and a signal-to-noise ratio in the visualization of deep sites. For the lower extremities, Examples 1 to 5 have a higher visualization score than Comparative Examples 1 to 10, which results indicate excellent visualization uniformity from shallow to deep sites.

In the ultrasound image diagnostic apparatus S according to this embodiment, the transmitter 12 generates an excitation signal and outputs it to the ultrasound probe 2 to instruct the ultrasound probe 2 to generate ultrasound. The receiver 13 receives a detected signal from the ultrasound probe 2. The image generator 14 extracts harmonic components from the received signal and generates ultrasound image data based on the harmonic components. The transmitter 12 activates and instructs the ultrasound probe 2 to transmit ultrasound with the excitation signal. The ultrasound satisfies the following requirements: The wave packet duration is equivalent to or more than the length of 1.5 waveforms at the lower limit frequency of the −6 dB transmission bandwidth of the ultrasound probe 2; the signal intensity of frequency components in the −6 dB transmission bandwidth has a standard deviation of 6 or less; and the signal intensity, normalized with respect to the maximum intensity of 0 [dB], of lower limit frequency components in the −6 dB transmission bandwidth is −8 [dB] or higher. The image generator 14 receives a reception signal in response to the transmission of the ultrasound and generates ultrasound image data based on harmonic components of the received signal.

This configuration can maintain a high resolution and a high signal-to-noise ratio of ultrasound images generated for shallow sites from ultrasound image data, increase the penetration depth, enhance the resolution of the ultrasound image for shallow and deep sites (prevent a significant reduction in resolution), and achieve visualization uniformity from the shallow to deep sites, without increasing the driving voltage or using a pulse compression technique, thus facilitating the acquisition of a highly uniformed and high-quality ultrasound image for the shallow to deep sites.

The transmitter 12 of the ultrasound image diagnostic apparatus S uses an excitation signal that satisfies the following requirements to activate and instruct the ultrasound probe 2 to generate harmonic reception signal: The excitation time is equivalent to or more than the length of 1.5 waveforms at the lower limit frequency of the −6 dB transmission bandwidth of the ultrasound probe 2; the signal intensity of the frequency components in the −6 dB transmission bandwidth has a standard deviation of 7 or less; and the signal intensity of lower limit frequency components in the −6 dB transmission bandwidth is 10 [dB] or higher.

This configuration can maintain a high resolution and a high signal-to-noise ratio of ultrasound images generated for shallow sites from ultrasound image data, increase the penetration depth, enhance the resolution of the ultrasound image for shallow and deep sites (prevent a significant reduction in resolution), and achieve visualization uniformity from the shallow to deep sites, without increasing the driving voltage or using a pulse compression technique, thus facilitating the acquisition of a highly uniformed and high-quality ultrasound image for the shallow to deep sites.

The transmitter 12 synthesizes multiple AM- or FM-modulated temporal waveforms to generate an excitation signal. This allows the transmitter 12 to generate an excitation signal that generates ultrasound having frequency components that generate harmonic components for both shallow and deep sites as shown in FIG. 6A.

The transmitter 12 synthesizes multiple AM- or FM-modulated temporal waveforms into a waveform, assigns voltage to the synthesized waveform in accordance with the number of voltage levels of the transmitter, memorizes the waveform information, and generates an excitation signal based on the memorized waveform information. This operation allows the transmitter 12 to generate an excitation signal that generates ultrasound having frequency components that generate harmonic components for both shallow and deep sites as shown in FIG. 6A.

The transmitter 12 of the ultrasound image diagnostic apparatus S uses an excitation signal that satisfies the following requirements to activate and instruct the ultrasound probe 2 to generate harmonic reception signal: The excitation time is equivalent to or more than the length of 1.5 waveforms at the lower limit frequency of the −6 dB transmission bandwidth of the ultrasound probe 2; the duration of parts of the excitation signal is converted into a frequency with the duration of each part regarded as 0.5 waveforms and the converted frequency is normalized with respect to the central frequency FC6 of the −6 dB transmission and reception bandwidth, and the normalized frequency has a standard deviation ranging from 0.1 to 0.3.

This configuration can maintain a high resolution and a high signal-to-noise ratio of ultrasound images generated for shallow sites from ultrasound image data, increase the penetration depth, enhance the resolution of the ultrasound image for shallow and deep sites (prevent a significant reduction in resolution), and achieve visualization uniformity from the shallow to deep sites, without increasing driving voltage or using a pulse compression technique, thus facilitating the acquisition of a highly uniformed and high-quality ultrasound image for the shallow to deep sites.

At least one of the first and last parts of the excitation time is the maximum part in all the parts. This fact facilitates the acquisition of ultrasound having high-frequency components localized as shown in FIG. 6A.

All the parts between the first and last parts of the excitation time are shorter than the first and last parts. This fact facilitates the acquisition of ultrasound having high-frequency components localized as shown in FIG. 6A.

The transmitter 12 outputs multiple excitation signals having different waveforms at certain intervals on one scanning line. Reception signals are created in response to the reflected ultrasound corresponding to the ultrasound generated in response to the multiple excitation signals. The image generator 14 extracts harmonic components through calculation of the reception signals and generates ultrasound image data based on the harmonic components. This allows a high-resolution ultrasound image, from which unnecessary frequency components are removed, to be acquired.

The above preferred embodiment is an exemplary embodiment of the ultrasound image diagnostic apparatus according to the present invention and the apparatus may have any other embodiments.

Any components or operations of the ultrasound image diagnostic apparatus S according to this embodiment can be suitably modified without departure of the scope of the present invention.

This U.S. patent application claims priority to Japanese patent application No. 2015-103842 filed on May 21, 2015, the entire contents of which are incorporated by reference herein for correction of incorrect translation.

What is claimed is:

1. An ultrasound image diagnostic apparatus comprising:
an ultrasound probe which transmits ultrasound to a subject, receives reflected ultrasound, and generates a reception signal;
a transmitter which generates an excitation signal and outputs the excitation signal to the ultrasound probe to instruct the ultrasound probe to generate the transmitted ultrasound;
a receiver which receives the reception signal from the ultrasound probe; and
an image generator which extracts harmonic components from the reception signal and generates ultrasound image data based on the harmonic components,
wherein the transmitter drives the ultrasound probe with the excitation signal to instruct the ultrasound probe to transmit the transmitted ultrasound that satisfies the following requirements: a wave packet duration is equivalent to or more than the length of 1.5 waveforms at the lower limit frequency of the −6 dB transmission bandwidth of the ultrasound probe; signal intensity of frequency components in the −6 dB transmission bandwidth has a standard deviation of 6 or less; and lower limit frequency components in the −6 dB transmission bandwidth have a signal intensity of −8 [dB] or higher, the signal intensity being normalized with respect to the maximum intensity of 0 [dB], and wherein the image generator generates the ultrasound image data based on the harmonic components in the reception signal obtained after the transmission of the transmitted ultrasound.

2. The ultrasound image diagnostic apparatus according to claim 1, wherein the transmitter synthesizes AM- or FM modulated multiple temporal waveforms into the excitation signal.

3. The ultrasound image diagnostic apparatus according to claim 1, wherein the transmitter assigns voltage to a waveform into which AM- or FM modulated multiple temporal waveforms are synthesized in accordance with the number of voltage levels of the transmitter, stores waveform information, and generates the excitation signal based on the stored waveform information.

4. The ultrasound diagnostic apparatus according to claim 1,
wherein the transmitter outputs multiple excitation signals having different waveforms at certain intervals on one scanning line; and
wherein the image generator extracts the harmonic components through calculation of reception signals generated in response to reflected ultrasound corresponding to ultrasound generated in response to the multiple excitation signals, and generates the ultrasound image data based on the harmonic components.

5. An ultrasound image diagnostic apparatus comprising:
an ultrasound probe which transmits ultrasound to a subject, receives reflected ultrasound, and generates a reception signal;
a transmitter which generates an excitation signal and outputs the excitation signal to the ultrasound probe to instruct the ultrasound probe to generate the transmitted ultrasound;
a receiver which receives the reception signal from the ultrasound probe; and
an image generator which extracts harmonic components from the reception signal and generates ultrasound image data based on the harmonic components,
wherein the transmitter drives the ultrasound probe with the excitation signal that satisfies the following requirements: excitation time is equivalent to or more than the length of 1.5 waveforms at the lower limit frequency of the −6 dB transmission bandwidth of the ultrasound probe, signal intensity of frequency components in the −6 dB transmission bandwidth has a standard deviation of 7 or less; and signal intensity of lower limit frequency components in the −6 dB transmission bandwidth is 10 [dB] or higher.

6. An ultrasound image diagnostic apparatus comprising:
an ultrasound probe which transmits ultrasound to a subject, receives reflected ultrasound, and generates a reception signal;
a transmitter which generates an excitation signal and outputs the excitation signal to the ultrasound probe to instruct the ultrasound probe to generate the transmitted ultrasound;
a receiver which receives the reception signal from the ultrasound probe; and
an image generator which extracts harmonic components from the reception signal and generates ultrasound image data based on the harmonic components,
wherein the transmitter drives the ultrasound probe with the excitation signal that satisfies the following requirements: excitation time is equivalent to or more than the length of 1.5 waveforms at the lower limit frequency of the −6 dB transmission bandwidth of the ultrasound probe, duration of parts of the excitation signal is converted into a frequency with duration of each of the parts regarded as 0.5 waveforms, the converted frequency is normalized with respect to the central frequency of the −6 dB transmission and reception bandwidth of the ultrasound probe, and the normalized frequency has a standard deviation ranging from 0.1 to 0.3.

7. The ultrasound diagnostic apparatus according to claim 6, wherein at least one of a first part and a last part of the excitation time is the maximum part of all parts.

8. The ultrasound diagnostic apparatus according to claim 7, wherein all parts between the first and the last parts of the excitation time are shorter than both the first and last parts.

* * * * *